United States Patent
Xin et al.

(10) Patent No.: US 7,169,797 B2
(45) Date of Patent: Jan. 30, 2007

(54) PROTEIN-TYROSINE PHOSPHATASE INHIBITORS AND USES THEREOF

(75) Inventors: Zhili Xin, Lake Bluff, IL (US); Gang Liu, Gurnee, IL (US); Zhonghua Pei, Libertyville, IL (US); Bruce G. Szczepankiewicz, Lindenhurst, IL (US); Michael D. Serby, Mundelein, IL (US); Hongyu Zhao, Buffalo Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 211 days.

(21) Appl. No.: 10/771,926

(22) Filed: Feb. 4, 2004

(65) Prior Publication Data

US 2004/0214870 A1    Oct. 28, 2004

Related U.S. Application Data

(60) Provisional application No. 60/447,407, filed on Feb. 14, 2003.

(51) Int. Cl.
| | |
|---|---|
| A61K 31/445 | (2006.01) |
| A61K 31/41 | (2006.01) |
| C07D 211/32 | (2006.01) |
| C07D 285/12 | (2006.01) |
| C07D 271/06 | (2006.01) |

(52) U.S. Cl. ............... 514/330; 514/331; 514/362; 514/365; 514/374; 514/381; 514/383; 546/189; 548/136; 548/143; 548/202; 548/206; 548/215; 548/240; 548/262; 548/335.5

(58) Field of Classification Search ............... 548/136, 548/143, 252, 262.2, 335.5, 202, 206, 215, 548/240; 514/362, 383, 330, 381, 365, 331, 514/374, 364; 546/189
See application file for complete search history.

(56) References Cited

FOREIGN PATENT DOCUMENTS

| WO | 0117516 | 3/2001 |
|---|---|---|
| WO | 0119830 | 3/2001 |
| WO | 0119831 | 3/2001 |

OTHER PUBLICATIONS

Barret et al., Solid-phase Synthesis of Isoxazoles Using Vinyl Ethers as Chameleon Catches, Organic Latter, vol. 3, No. 20, pp. 3165-3168.*
Ahmad, F., et al., "Osmotic Loading of Neutralizing Antibodies Demonstrates a Role for Protein-tyrosine Phosphatase 1B in Negative Regulation of the Insulin Action Pathway (*)",Jour. Biol. Chem, 270(35):20503-20508 (1995.
Bryant, N. J., et al., "Regulated Transport of the Glucose Transporter Glut4", Nature Reviews. 3:267-277 (2002).
Cheng, A., et al., "Coordinated action of protein tyrosine phosphatases in insulin signal transduction", Eur. J. Biochem., 269:1050-1059 (2002).

Dunstan, D. W., et al., "The Rising Prevalence of Diabetes and Impaired Glucose Tolerance: The Australian Diabetes, Obesity and Lifestyle Study", Diabetes Care, 25(5)829-834 (2002).
Elchebly, M., et al., "Increased Insulin Sensitivity and Obesity Resistance in Mice Lacking the portein Tyrosine Phosphatase-1B Gene", Science, 283:1544-1548 (1999).
Flint, A. J., et al., "Multi-site phosphorylation of the protein tyrosine phosphatase, PTP1B: identification of cell cycle regulated and phorbol ester stimulated sites of phosphorylation", The EMBO Jour., 12(5)1937-1946 (1993).
Goldstein, B. J., et al., "Tyrosine Dephosphorylation and Deactivation of Insulin Receptor Substrate-1 by Protein-tyrosine Phosphatase 1B", Jour. Biol. Chem., 275(6):4283-4289 (2000).
Groop, L. & Orho-Melander, M., "The dysmetabolic syndrome", Jour. of Internal Med., 250:105-120 (2001).
Klaman, L. D., et al., "Increased Energy Expenditure, Decreased Adiposity, and Tissue-Specific Insulin Sensitivity in Protein-Tyrosine Phosphatase 1B-Deficient Mice", Molecular and Cellular Biol., 20(15):5479-5489 (2000).
Mauro, L. J., et al., "Identification of a Hormonally Regulated Protein Tyrosine Phosphatase Associated with Bone and Testicular Differentiation", The Journ. of Biol. Chem., 269:30659-30667 (1994).
Noguchi, T., et al., "Role of SH-PTP2, a Protein-Tyrosine Phosphatase with Src Homology 2 Domains, in Insulin-Stimulated Ras Activation", Mol. and Cell. Biol., 14(10):6674-6682 (1994).
Ostman, A. & Böhmer, F-D., "Regulation of receptor tyrosine kinase signaling by protein tyrosine phosphatases", Trends Cell Biol., 11:258-266 (2001).
Saltiel, A. R., & Pessin, J. E., "Insulin signaling pathways in time and space", Treands in Cell Biol., 12(2):65-71 (2001).

(Continued)

Primary Examiner—Kamal A. Saeed
Assistant Examiner—Ebenezer Sackey
(74) Attorney, Agent, or Firm—Johanna M. Corbin

(57) ABSTRACT

The present invention is directed to compounds of formula (I),

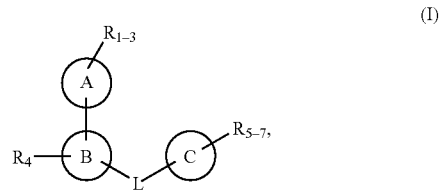

or a pharmaceutically suitable salt or prodrug thereof, which are useful for the selective inhibition of protein tyrosine phosphatase-1B (PTP1B), and are useful for the treatment of disorders caused by overexpressed or altered protein tyrosine phosphatase 1B.

12 Claims, No Drawings

OTHER PUBLICATIONS

Seely, L. B., et al., "Protein Tyrosine Phosphatase 1B Interacts With the Activated Insulin Receptor", *diabetes*, 4(10):1379-1385 (1996).

Wang, Q., et al., "Mechanism of Inhibition of Protein-Tyrosine Phosphatases by Disodium Aurothiomalate", *Biochem. Pharma.*, 54:703-711 (1997).

Wiener, J. R., et al., "Overexpression of the Protein Tyrosine Phosphatase PTP1B in Human Breast Cancer: Association With p185[c-erbB-2] Protein Expression", *Journ of the Nat'l Cancer Insti.*, 86(5):372-378 (1994).

Zabolotny, J. M., et al., "PTO1B Regulates Leptin Signal Transduction in ViVo", *Developmental Cell*, 2:489-495 (2002).

Zinker, B. A., et al., "PTP1B antisense oligonucleotide lowers PTO1B protein, normalizes blood glucose, and improves insulin sensitivity indiabetic mice", *Proc. Natl. Acad. Sci. USA*, 99(17):11357-11362 (2002).

* cited by examiner

PROTEIN-TYROSINE PHOSPHATASE INHIBITORS AND USES THEREOF

This application claims priority to the provisional application Ser. No. 60/447,407 filed on Feb. 14, 2003.

TECHNICAL FIELD

The present invention is directed to compounds useful for the selective inhibition of protein tyrosine phosphatase-1B (PTP1B), preparation of the compounds, compositions containing the compounds and the treatment of disorders using the compounds.

BACKGROUND OF THE INVENTION

PTP1B and the Insulin Receptor Signaling Pathway/Diabetes and Obesity

The increased incidence of type 2 diabetes mellitus (T2DM) and obesity in the population has fueled an intensified search for new therapeutic treatment options. The relationship between T2DM and obesity has a polygenetic component and is associated with insulin resistance and impaired glucose tolerance (IGT) (Dunstan, D. W. et al. *Diabetes Care* 25, 829–834 (2002); Groop et al., *J. Int. Med.* 250, 105–120 (2001)).

Insulin resistance is evident in many tissues that are important for glucose homeostasis including muscle, liver and more recently in fat and at the level of the central nervous system in diabetic patients. Metabolic insulin signal transduction occurs through activation of the insulin receptor, including autophosphorylation of tyrosine (Tyr) residues in the insulin-receptor activation loop (Saltiel & Pessin, *Trends Cell Biol.* 12, 65–71 (2002)). This leads to recruitment of insulin-receptor substrate (IRS) proteins, followed by activation of phosphatidylinositol 3-kinase (PI3K) and downstream protein kinase B (PKB; also known as AKT), and activation and subsequent translocation of the glucose transporter GLUT4 (Bryant et al., *Nature Rev. Mol. Cell Biol.* 3, 267–277 (2002)). This process is negatively regulated by protein tyrosine phosphatases (PTPases), and is a general mechanism for downregulation of receptor tyrosine kinase (RTK) activity (Ostman & Bohmer, *Trends Cell Biol.* 11, 258–266 (2001)). Several PTPases, including receptor protein tyrosine phosphatase-α (rPTP-α), leukocyte antigen-related tyrosine phosphatase (LAR), SH2-domain-containing phosphotyrosine phosphatase (SHP2) and protein tyrosine phosphatase 1B (PTP1B) have been implicated in modulating insulin signal transduction (Cheng et al., *Eur. J. Biochem.* 269, 1050–1059 (2002)). PTP1B seems to be a key regulator of insulin-receptor activity that acts at the insulin receptor and at downstream signaling components, such as IRS1 (Goldstein et al., *J. Biol. Chem.* 275, 4283–4289 (2000)).

PTP1B has been identified as at least one of the major phosphatases involved in the insulin RTK regulation through studies conducted both in vitro (Seely et al. *Diabetes* 45, 1379–1385 (1996)) and in vivo using PTP1B neutralizing antibodies (Ahmad et al. *J. Biol. Chem.* 270, 20503–20508 (1995)). Two independent studies have indicated that PTP 1B knock-out mice have increased glucose tolerance, increased insulin sensitivity and decreased weight gain on a high fat diet (Elchebly et al. *Science* 283, 1544–1548 (1999) and Klaman et al. *Mol. Cell. Biol.* 20, 5479–5489 (2000)). The increased insulin sensitivity that was found in PTP1B-deficient mice helped to validate this protein as a key negative regulator of insulin signal transduction. The ability of PTP1B to dephosphorylate several substrates with recognition motifs similar to those found in janus kinase 2 (JAK2), and what seemed to be an associated increase in leptin sensitivity, implied that PTP1B might be involved in regulating the leptin signaling pathway (Zabolotny, et al. *Dev. Cell* 2, 489–495 (2002)). These results indicate that PTP1B inhibition might be effective in reducing both leptin and insulin resistance. Inhibition of PTP1B in insulin target tissues using novel antisense oligonucoleotides has shown enhanced insulin signaling and glucose tolerance in preclinical diabetic rodent models (Zinker, et al. *Proc. Natl Acad. Sci. USA* 99, 11357–11362 (2002)). These studies strongly suggest inhibition of protein tyrosine phosphatase PTP1B is therapeutically beneficial for the treatment of T2DM and obesity.

Furthermore, there is evidence that suggests inhibition of protein tyrosine phosphatase PTP1B is therapeutically beneficial for the treatment of diseases such as, autoimmune disease, acute and chronic inflammation, osteoporosis and various forms of cancer (*J. Natl. Cancer Inst* 86: 372–378 (1994); *Mol. Cell. Biol.* 14: 6674–6682 (1994); *The EMBO J.*, 12: 1937–1946 (1993); *J. Biol. Chem.* 269: 30659–30667 (1994); and *Biochemical Pharmacology* 54: 703–711 (1997)).

Cellular Permeable, Selective Inhibition of PTP1B with Small Molecule-Based Agents Because of the important roles played by upregulated protein tyrosine phosphatase PTP1B in the disease states of T2DM, obesity, autoimmune disease, acute and chronic inflammation, osteoporosis and various forms of cancer, agents that inhibit this enzyme specifically may provide the desired therapeutic benefits without the unwanted side effects derived from inhibiting the related phosphatases.

A panel of different phosphatases is selected for assaying the different inhibitory activities exhibited by the claimed agents. These phosphatases are selected on the basis of their homology to PTP1B, from the most homologous one, such as TCPTP, to the somewhat homologous phosphatase, such as SHP-2 and LAR, to the least homologous ones, such as cdc25c, CD45 and PP2B. Reference is made to WO 01/19831, WO 01/19830, WO 01/17516; and although each disclose certain heteroaryl and aryl amino(oxo)acetic acid protein tyrosine phosphatase PTP1B inhibitors, there is no separation of the inhibitory activity exhibited by the claimed agents between PTP1B and TCPTP. Because of the potential immunosuppressive effect derived from inhibiting TCPTP, the instant invention provides PTP1B inhibitors which demonstrated consistently greater than twenty-fold selective inhibitory activity for PTP1B over TCPTP, making them more suitable for drug development. The specificity against the other phosphatases in the panel is the range of 30 fold to 2,800 fold, which should be sufficient to offer a useful therapeutic window.

PTP1B inhibitors need to have good cellular penetration, as the target is intracellular, and an orally available drug is desired. This is a formidable challenge because of the physical nature of this protein target. The catalytic site complements a negatively charged phosphopeptide and the remainder of the active site is exposed to solvent. To gain potency, inhibitors of these types of target tend to be large molecules that have a multiple charge (Reference is made to WO 01/19831, WO 01/19830, WO 01/17516). This instant invention provides PTP1B inhibitors with only one carboxylic acid as the phosphotyrosine mimetic. Such a structural feature rendered the inhibitors with good cellular penetration in a Caco-2 permeability assay. More importantly, in a Cos7 cellular assay measuring the intracellular inhibition of PTP1B, these inhibitors demonstrated robust inhibitory activity against intracellular PTP1B. These advancements should make these inhibitors better suited as orally deliverable therapeutic agents.

SUMMARY OF THE INVENTION

The present invention is directed to compounds of formula (I),

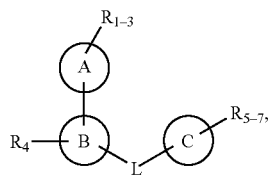

or a pharmaceutically suitable salt or prodrug thereof, wherein

A is a member selected from the group consisting of

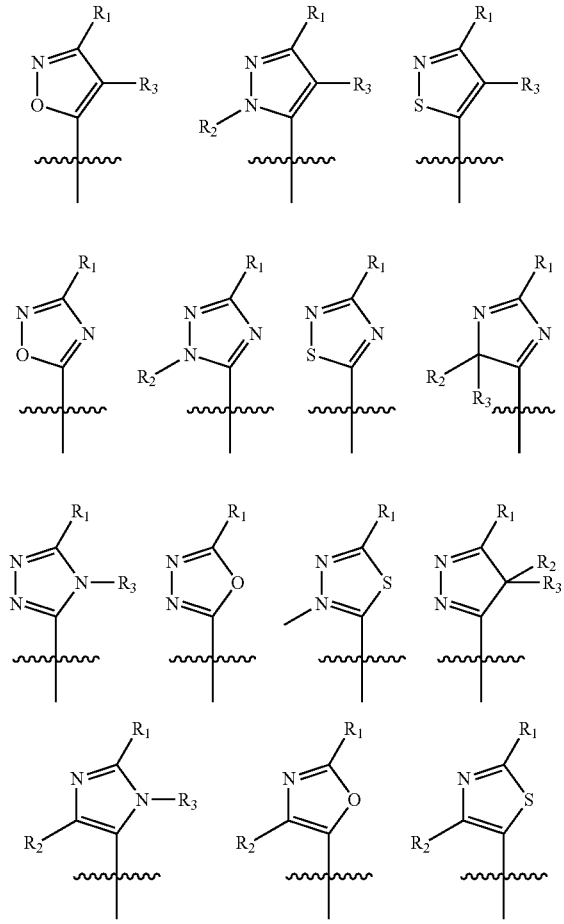

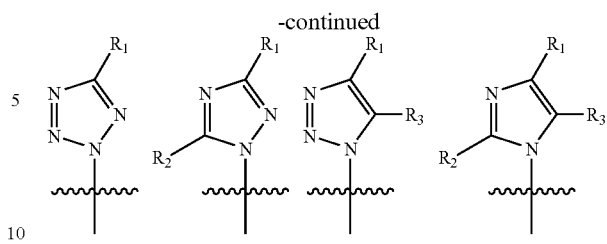

B and C are each independently a member selected from the group consisting of aryl, and heterocycle;

$R_1$ is a member selected from the group consisting of alkyl, alkoxy, alkylSO$_2$, trifluoroalkylSO$_2$, trifluoroalkylNH—, alkylSO$_2$NH—, carboxy, cyano, HONHcarbonyl, $R_a$ONHcarbonyl, nitro, $R_a$OC(O)—, HO$_3$S—, H$_2$NO$_2$S—, $R_a$NHO$_2$S—, (HO)$_2$(O)P—, (HO)$_2$(O)PCH$_2$—, (HO)$_2$(O)PCHF—, (HO)$_2$(O)PCF$_2$— and heterocycle, wherein said heterocycle is a member selected from the group consisting of:

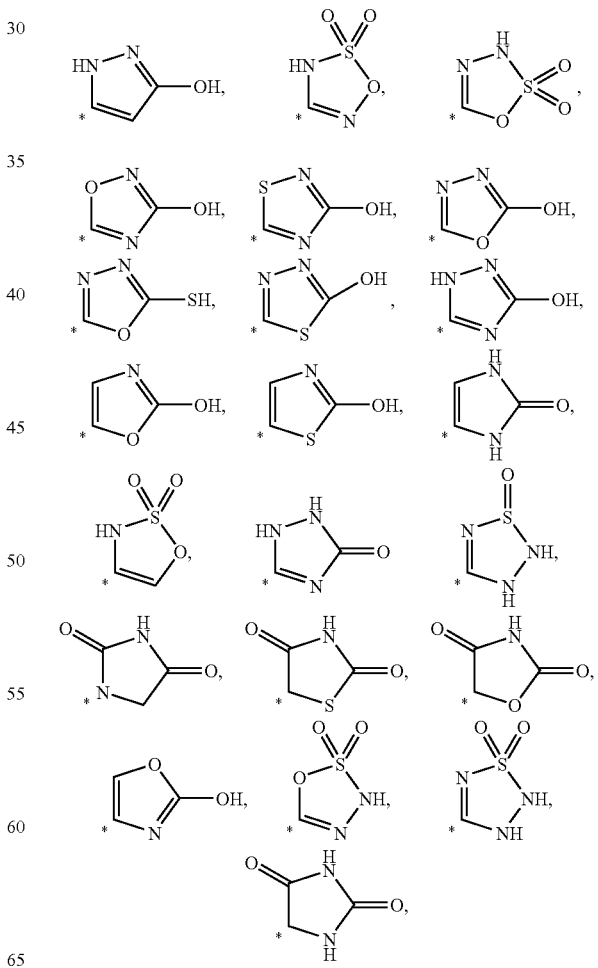

$R_2$, $R_3$, $R_4$, $R_5$, $R_6$ and $R_7$ are each independently absent or are independently a member selected from the group consisting of hydrogen, alkyl, alkylcarbonyl, alkoxy, alkoxyalkyl, alkoxycarbonyl, aryl, arylcarbonyl, arylalkyl, carboxy, carboxyalkyl, cyano, cycloalkyl, cycloalkylalkyl, halo, haloalkyl, heterocycle, heterocyclecarbonyl, heterocyclealkyl, hydroxy, hydroxyalkyl, nitro, trihaloalkyl, $R_aR_bN$, $R_aR_bN$alkyl, $R_aR_b$Ncarbonyl, $R_aR_b$Ncarbonylalkyl, $R_aR_b$NNsulfonyl, $R_aR_b$NNsulfonylalkyl, wherein $R_a$ and $R_b$ are each independently a member selected from the group consisting of hydrogen, alkyl, alkoxycarbonyl, alkylcarbonyl, aryl, arylalkyl, cycloalkyl, cycloalkylalkyl, heterocycle, and heterocyclealkyl;

L is -G-$X_1$-J-$X_2$—K— or a bond;

G, J and K are independently a member selected from the group consisting of a bond, alkyl, alkenyl, aryl and cycloalkyl, wherein said alkyl, alkenyl, aryl and cycloalkyl may be optionally substituted with a group consisting of alkoxy, alkyl, halogen, hydroxy, hydroxyalkyl, carboxy and $R_dR_eN$—, wherein $R_d$ and $R_e$ are each independently a member selected from the group consisting of hydrogen, alkyl, alkoxycarbonyl, alkylcarbonyl and arylalkyl;

$X_1$ and $X_2$ are each independently a member selected from the group consisting of a bond, —O—, —N($R_c$)—, —N($R_c$)C(O)—, —C(O)N($R_c$)—, —N($R_c$)S(O)$_2$—, —S(O)$_2$N($R_c$)—, and —C(O)—, wherein $R_c$ is a member selected from the group consisting of hydrogen, alkyl and arylalkyl; and provided that if J is absent, then at least one of $X_1$ and $X_2$ must be absent.

According to an embodiment, the present invention is directed to a pharmaceutical composition comprising a therapeutically effective amount of a compound of formula (I) in combination with a pharmaceutically suitable carrier.

According to another embodiment, the present invention is directed to method of selectively inhibiting protein tyrosine phosphatase 1B comprising administering a therapeutically effective amount of a compound of formula (I) in combination with a pharmaceutically suitable carrier.

According to another embodiment, the present invention is directed to a method of treating disorders caused by overexpressed or altered protein tyrosine phosphatase 1B comprising administering a therapeutically effective amount of a compound of formula (I) in combination with a pharmaceutically suitable carrier.

According to another embodiment, the present invention is directed to a method of treating type I and type II diabetes, impaired glucose tolerance and insulin resistance, comprising administering a therapeutically effective amount of a compound of formula (I) in combination with a pharmaceutically suitable carrier.

According to another embodiment, the present invention is directed to a method of treating obesity comprising administering a therapeutically effective amount of a compound of formula (I) in combination with a pharmaceutically suitable carrier.

According to another embodiment, the present invention is directed to a method of treating autoimmune disorders, acute and chronic inflammatory disorders, osteoporosis, cancer, malignant disorders comprising administering a therapeutically effective amount of a compound of formula (I) in combination with a pharmaceutically suitable carrier.

DETAILED DESCRIPTION OF THE INVENTION

All U.S. Patents and publications are hereby incorporated herein, in their entirety, by reference.

Definitions

As used throughout the present specification, the following terms have the meanings indicated:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "aryl," as used herein, refers to a dihydronaphthyl, indanyl, indenyl, naphthyl, phenyl, and tetrahydronaphthyl. Aryl groups having an unsaturated or partially saturated ring fused to an aromatic ring can be attached through the saturated or the unsaturated part of the group. The aryl groups of the present invention can be substituted with 0, 1, 2, 3, 4 or 5 substituents independently a member selected from the group consisting of alkenyl, alkoxy, alkoxycarbonyl, alkyl, alkylsufonyl, alkylthio, alkynyl, carboxy, carboxyalkenyl, carboxyalkyl, cyano, halo, haloalkyl, haloalkoxy, hydroxy, hydroxyalkyl, nitro, $R_aR_bN$—, $R_aR_bNC(O)$—, $R_aR_bN$alkyl, and $R_aR_bNS(O)_2$—, where $R_a$ and $R_b$ are each independently a member selected from the group consisting of hydrogen, alkyl, alkoxycarbonyl, alkylcarbonyl, aryl, arylalkyl, cycloalkyl, cycloalkylalkyl, heterocycle, and heterocyclealkyl, or $R_a$ and $R_b$ together with the nitrogen to which they are attached form a ring a member selected from the group consisting of azetidine, pyrrolidine, piperidine, morpholine, piperazine and thiozolidine. The aryl groups of this invention can be further substituted with an additional aryl group, an arylalkyl group, an arylcarbonyl group or a heterocycle, as defined herein, wherein the additional aryl group and the heterocycle can be substituted with 1, 2 or 3 substituents independently a member selected from of alkoxy, alkoxycarbonyl, alkyl, alkylsufonyl, carboxy, carboxyalkyl, cyano, halo, haloalkyl, hydroxy, hydroxyalkyl, nitro, $R_aR_bN$—, $R_aR_bNC(O)$—, where $R_a$ and $R_b$ are previously defined.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylcarbonyl," as used herein, refers to an arylalkyl group, as defined herein, appended to the parent molecular moiety through a carbonyl group, as defined herein. Representative examples of arylalkylcarbonyl include, but are not limited to, phenylacetyl and 3-phenylpropanoyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, 4-cyanobenzoyl, and naphthoyl.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "carbonyl," as used herein, refers to a —C(O)—.

The term "carboxy," as used herein, refers to a —$CO_2H$.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN.

The term "cycloalkyl," as used herein, refers to a monovalent saturated cyclic or bicyclic hydrocarbon group of three to twelve carbons. The cycloalkyl groups of the invention can be substituted with 0, 1, 2, 3 or 4 substituents independently a member selected from the group consisting of alkylcarbonyl, alkoxy, alkoxycarbonyl, alkyl, carboxy, halo and hydroxy, hydroxyalkyl, $R_aR_bN$—, $R_aR_bNC(O)$— and $R_aR_bN$alkyl.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "halo," refers to an F, Cl, Br, or I.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "heterocycle" or "heterocyclic," as used herein, refers to a monocyclic or bicyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered rings have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another heterocyclic monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl.

The heterocycles of this invention can be substituted with 0, 1, 2, 3, 4 or 5 substituents independently a member selected from the group consisting of alkenyl, alkoxy, alkoxycarbonyl, alkyl, alkylsufonyl, alkylthio, alkynyl, carboxy, carboxyalkenyl, carboxyalkyl, cyano, halo, haloalkyl, haloalkoxy, hydroxy, hydroxyalkyl, nitro, $R_aR_bN$—, $R_aR_bNC(O)$—, $R_aR_bN$alkyl, and $R_aR_bNS(O)_2$—, where $R_a$ and $R_b$ are defined herein. The heterocycle groups of this invention can be further substituted with an aryl group, an arylalkyl group, an arylcarbonyl group or an additional heterocycle, as defined herein, wherein the aryl groups and the additional heterocycle can be substituted with 1, 2 or 3 substituents independently a member selected from the group consisting of alkoxy, alkoxycarbonyl, alkyl, alkylsufonyl, alkylthio, carboxy, carboxyalkenyl, carboxyalkyl, cyano, halo, haloalkyl, haloalkoxy, hydroxy, hydroxyalkyl, nitro, $R_aR_bN$—, $R_aR_bNC(O)$—, $R_aR_bN$alkyl, and $R_aR_bNS(O)_2$—, where $R_a$ and $R_b$ are defined herein.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "hydroxy," as used herein, refers to an —OH.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "nitro," as used herein, refers to a —NO$_2$.

The term "trihaloalkyl," as used herein, refers to at least an alkyl group, as defined herein substituted with 3 halogens, as defined herein. Representative examples of trihaloalkyl include, but are not limited to, trichloromethyl, 2-trifluoroethyl, trifluoromethyl, and 2-chloro-3-difluoropentyl.

The present invention provides compounds which selectively inhibit protein tyrosine phosphatase (PTP1B). In particular, the compounds of the present invention are selective PTP1B inhibitors and therefore are useful for treating disorders caused by overexpressed or altered protein tyrosine phosphatase (PTP1B). These disorders include, for example, autoimmune disorders, acute and chronic inflammatory disorders, osteoporosis, obesity, cancer, malignant disorders, and type I and type II diabetes.

Accordingly the principle embodiment of the present invention is directed to compounds of formula (I),

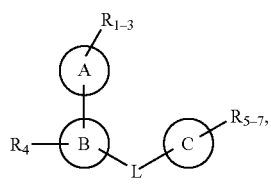
(I)

or a pharmaceutically suitable salt or prodrug thereof, wherein

A is a member selected from the group consisting of

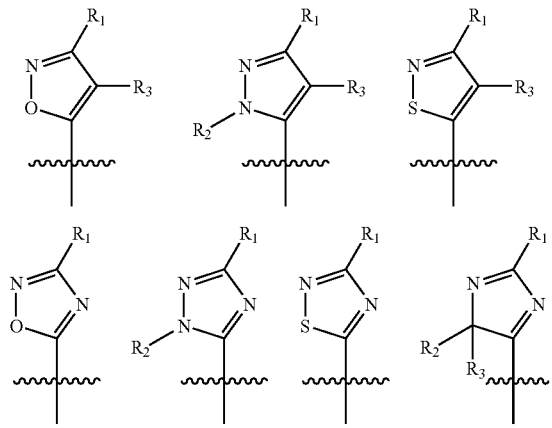

B and C are each independently a member selected from the group consisting of aryl, and heterocycle;

$R_1$ is a member selected from the group consisting of alkyl, alkoxy, alkylSO$_2$, trifluoroalkylSO$_2$, trifluoroalkylNH—, alkylSO$_2$NH—, carboxy, cyano, HONHcarbonyl, R$_a$ONHcarbonyl, nitro, R$_a$OC(O)—, HO$_3$S—, H$_2$NO$_2$S—, R$_a$NHO$_2$S—, (HO)$_2$(O)P—, (HO)$_2$(O)PCH$_2$—, (HO)$_2$(O)PCHF—, (HO)$_2$(O)PCF$_2$— and heterocycle, wherein said heterocycle is a member selected from the group consisting of:

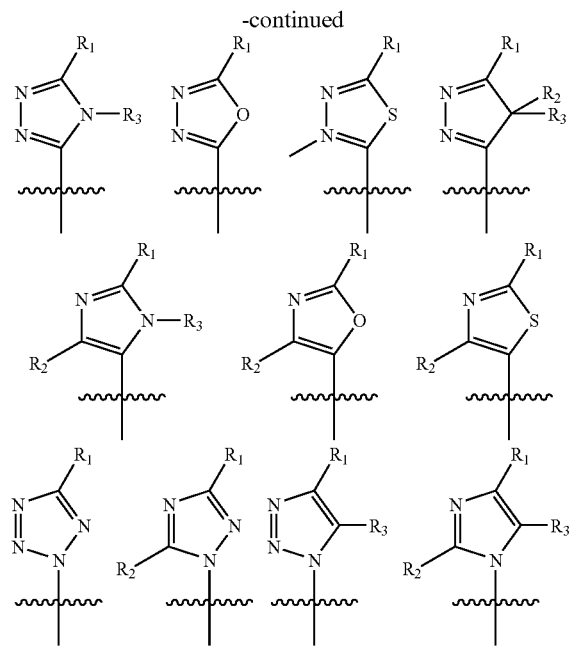

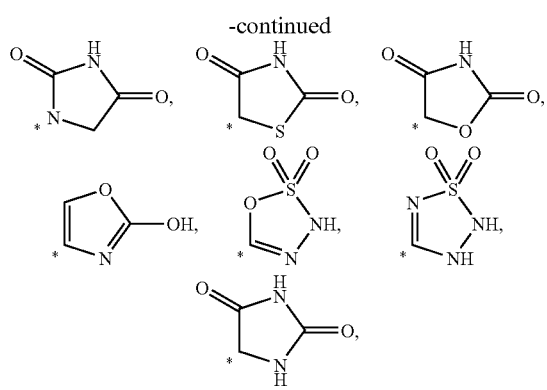

$R_2$, $R_3$, $R_4$, $R_5$, $R_6$ and $R_7$ are each independently absent or are independently a member selected from the group consisting of hydrogen, alkyl, alkylcarbonyl, alkoxy, alkoxyalkyl, alkoxycarbonyl, aryl, arylcarbonyl, arylalkyl, carboxy, carboxyalkyl, cyano, cycloalkyl, cycloalkylalkyl, halo, haloalkyl, heterocycle, heterocyclecarbonyl, heterocyclealkyl, hydroxy, hydroxyalkyl, nitro, trihaloalkyl, $R_aR_bN$, $R_aR_b$Nalkyl, $R_aR_b$Ncarbonyl, $R_aR_b$Ncarbonylalkyl, $R_aR_b$NNsulfonyl, $R_aR_b$NNsulfonylalkyl, wherein $R_a$ and $R_b$ are each independently a member selected from the group consisting of hydrogen, alkyl, alkoxycarbonyl, alkylcarbonyl, aryl, arylalkyl, cycloalkyl, cycloalkylalkyl, heterocycle, and heterocyclealkyl;

L is -G-$X_1$-J-$X_2$—K— or a bond;

G, J and K are independently a member selected from the group consisting of a bond, alkyl, alkenyl, aryl and cycloalkyl, wherein said alkyl, alkenyl, aryl and cycloalkyl may be optionally substituted with a group consisting of alkoxy, alkyl, halogen, hydroxy, hydroxyalkyl, carboxy and $R_dR_eN$— wherein $R_d$ and $R_e$ are each independently a member selected from the group consisting of hydrogen, alkyl, aLkoxycarbonyl, alkylcarbonyl and arylalkyl;

$X_1$ and $X_2$ are each independently a member selected from the group consisting of a bond, —O—, —N($R_c$)—, —N($R_c$)C(O)—, —C(O)N($R_c$)—, —N($R_c$)S(O)$_2$—, —S(O)$_2$N($R_c$)—, and —C(O)—, wherein $R_c$ is a member selected from the group consisting of hydrogen, alkyl and arylalkyl; and provided that if J is absent, then at least one of $X_1$ and $X_2$ must be absent.

According to another embodiment, the present invention is directed to compounds of formula (II)

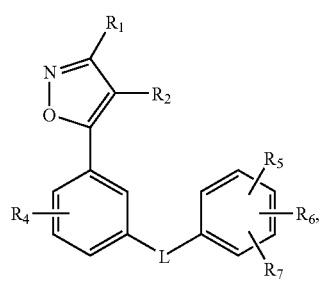

(II)

or a pharmaceutically suitable salt or prodrug thereof, wherein $R_1$ is a member selected from the group consisting of alkyl, alkoxy, alkylSO$_2$, trifluoroalkylSO$_2$, trifluoroalkylNH—, alkylSO$_2$NH—, carboxy, cyano, HONHcarbonyl, $R_a$ONHcarbonyl, nitro, $R_a$OC(O)—, HO$_3$S—, H$_2$NO$_2$S—, $R_a$NHO$_2$S—, (HO)$_2$(O)P—, (HO)$_2$(O)PCH$_2$—, (HO)$_2$(O)PCHF—, (HO)$_2$(O)PCF$_2$— and heterocycle, wherein said heterocycle is a member selected from the group consisting of:

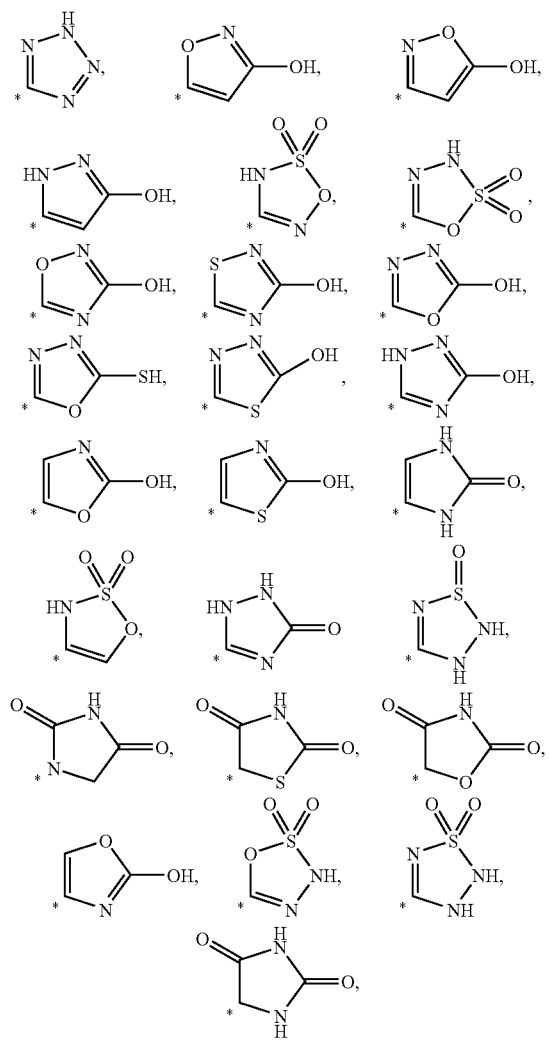

$R_2$, $R_3$, $R_4$, $R_5$, $R_6$ and $R_7$ are each independently absent or are independently a member selected from the group consisting of hydrogen, alkyl, alkylcarbonyl, alkoxy, alkokyalkyl, alkoxycarbonyl, aryl, arylcarbonyl, arylalkyl, carboxy, carboxyalkyl, cyano, cycloalkyl, cycloalkylalkyl, halo, haloalkyl, heterocycle, heterocyclecarbonyl, heterocyclealkyl, hydroxy, hydroxyalkyl, nitro, trihaloalkyl, $R_aR_bN$, $R_aR_b$Nalkyl, $R_aR_b$Ncarbonyl, $R_aR_b$Ncarbonylalkyl, $R_aR_b$NNsulfonyl, $R_aR_b$NNsulfonylalkyl, wherein $R_a$ and $R_b$ are each independently a member selected from the group consisting of hydrogen, alkyl, alkoxycarbonyl, alkylcarbonyl, aryl, arylalkyl, cycloalkyl, cycloalkylalkyl, heterocycle, and heterocyclealkyl;

L is —G—$X_1$—J—$X_2$—K— or is a bond;

G, J and K are independently a member selected from the group consisting of a bond, alkyl, alkenyl, aryl and cycloalkyl, wherein said alkyl, alkenyl, aryl and cycloalkyl may be optionally substituted with a group consisting of alkoxy, alkyl, halogen, hydroxy, hydroxyalkyl, carboxy and $R_dR_eN$—, wherein $R_d$ and $R_e$ are each independently a member selected from the group consisting of hydrogen, alkyl, alkoxycarbonyl, alkylcarbonyl and arylalkyl;

$X_1$ and $X_2$ are each independently a member selected from the group consisting of a bond, —O—, —N($R_c$)—, —N($R_c$)C(O)—, —C(O)N($R_c$)—, —N($R_c$)S(O)$_2$—, —S(O)$_2$N($R_c$)—, and —C(O)—, wherein $R_c$ is a member selected from the group consisting of hydrogen, alkyl and arylalkyl; and provided that if J is absent, then at least one of $X_1$ and $X_2$ must be absent.

According to a further embodiment of the present invention there is provided a compound of formula (II), wherein G is a member selected from the group consisting of alkyl, alkenyl and cycloalkyl, and wherein C, $R_1$, $R_2$ $R_3$, $R_4$, $R_5$, $R_6$, $R_7$, $R_a$, $R_b$, $R_c$, $R_d$, $R_e$, L, J, K, $X_1$, $X_2$, are as defined in formula (I).

According to a further embodiment of the present invention there is provided a compound of formula (II), wherein G is a member selected from the group consisting of alkyl, alkenyl and cycloalkyl, $X_1$, J and K are a bond, and wherein C, $R_1$, $R_2$ $R_3$, $R_4$, $R_5$, $R_6$, $R_7$, $R_a$, $R_b$, $R_c$, $R_d$, $R_e$, L, $X_2$, are as defined in formula (I).

According to a further embodiment of the present invention there is provided a compound of formula (II), wherein G is a member selected from the group consisting of alkyl, alkenyl and cycloalkyl, $X_1$, J and K are a bond, $R_1$ is $CO_2H$, and wherein C, $R_2$ $R_3$, $R_4$, $R_5$, $R_6$, $R_7$, $R_a$, $R_b$, $R_c$, $R_d$, $R_e$, L, $X_2$, are as defined in formula (I).

According to a further embodiment of the present invention there is provided a compound of formula (II), wherein G is a member selected from the group consisting of alkyl, alkenyl and cycloalkyl, $X_1$, J and K are a bond, $X_2$ is O, $R_1$ is $CO_2H$, and wherein C, $R_2$ $R_3$, $R_4$, $R_5$, $R_6$, $R_7$, $R_a$, $R_b$, $R_c$, $R_d$, $R_e$, L, $X_2$, are as defined in formula (I).

According to a further embodiment of the present invention there is provided a compound of formula (II), wherein $X_1$ is a member selected from the group consisting of —NH— and —NHC(O)—, and wherein C, $R_1$, $R_2$ $R_3$, $R_4$, $R_5$, $R_6$, $R_7$, $R_a$, $R_b$, $R_c$, $R_d$, $R_e$, L, G, J, K, $X_2$, are as defined in formula (I).

According to a further embodiment of the present invention there is provided a compound of formula (II), wherein $X_1$ is a member selected from the group consisting of —NH— and —NHC(O)—, G and K are a bond, and wherein C, $R_1$, $R_2$ $R_3$, $R_4$, $R_5$, $R_6$, $R_7$, $R_a$, $R_b$, $R_c$, $R_d$, $R_e$, L, J, $X_2$, are as defined in formula (I).

According to a further embodiment of the present invention there is provided a compound of formula (II), wherein $X_1$ is a member selected from the group consisting of —NH— and —NHC(O)—, G and K are a bond, $R_1$ is $CO_2H$, and wherein C, $R_2$ $R_3$, $R_4$, $R_5$, $R_6$, $R_7$, $R_a$, $R_b$, $R_e$, $R_d$, $R_e$, L, J, $X_2$, are as defined in formula (I).

According to a further embodiment of the present invention there is provided a compound of formula (II), wherein $X_1$ is a member selected from the group consisting of —NH— and —NHC(O)—, G and K are a bond, $X_2$ is O, $R_1$ is $CO_2H$, and wherein C, $R_1$, $R_2$ $R_3$, $R_4$, $R_5$, $R_6$, $R_7$, $R_a$, $R_b$, $R_c$, $R_d$, $R_e$, L and J are as defined in formula (I).

According to a further embodiment of the present invention there is provided a compound of formula (II), wherein L is a bond and wherein C, $R_1$, $R_2$ $R_3$, $R_4$, $R_5$, $R_6$, $R_7$, $R_a$, $R_b$, $R_c$, $R_d$ and $R_e$ are as defined in formula (I).

According to a further embodiment of the present invention there is provided a compound of formula (II), wherein L is a bond, $R_1$ is $CO_2H$ and wherein C, $R_2$ $R_3$, $R_4$, $R_5$, $R_6$, $R_7$, $R_a$, $R_b$, $R_c$, $R_d$ and $R_e$ are as defined in formula (I).

According to an embodiment, the present invention is directed to a pharmaceutical composition comprising a therapeutically effective amount of a compound of formula (I) in combination with a pharmaceutically suitable carrier.

According to another embodiment, the present invention is directed to method of selectively inhibiting protein tyrosine phosphatase 1B comprising administering a therapeutically effective amount of a compound of formula (I) in combination with a pharmaceutically suitable carrier.

According to another embodiment, the present invention is directed to a method of treating disorders caused by overexpressed or altered protein tyrosine phosphatase 1B comprising administering a therapeutically effective amount of a compound of formula (I) in combination with a pharmaceutically suitable carrier.

According to another embodiment, the present invention is directed to a method of treating type I and type II diabetes, impaired glucose tolerance and insulin resistance, comprising administering a therapeutically effective amount of a compound of formula (I) in combination with a pharmaceutically suitable carrier.

According to another embodiment, the present invention is directed to a method of treating obesity comprising administering a therapeutically effective amount of a compound of formula (I) in combination with a pharmaceutically suitable carrier.

According to another embodiment, the present invention is directed to a method of treating autoimmune disorders, acute and chronic inflammatory disorders, osteoporosis, cancer, malignant disorders comprising administering a therapeutically effective amount of a compound of formula (I) in combination with a pharmaceutically suitable carrier. Specific compounds of the present invention include, but are not limited to: 5-(3-((1E)-3-(3-hydroxy-2-(methoxycarbonyl)phenoxy)prop-1-enyl)phenyl)isoxazole-3-carboxylic acid;

5-(3-(3-(3-hydroxy-2-(methoxycarbonyl)phenoxy)butyl)phenyl)isoxazole-3-carboxylic acid;

5-(3-((2-(3-hydroxy-2-(methoxycarbonyl)phenoxy)ethyl)amino)phenyl)isoxazole-3-carboxylic acid;

5-(3-(((1-acetylpiperidin-4-yl)carbonyl)amino)phenyl)isoxazole-3-carboxylic acid;

5-(3-((2-(3-hydroxy-2-((methylamino)carbonyl)phenoxy)ethyl)amino)phenyl)isoxazole-3-carboxylic acid;

5-(3-((1E)-3-(3-hydroxy-2-((methylamino)carbonyl)phenoxy)prop-1-enyl)phenyl)isoxazole-3-carboxylic acid;

5-(3-(3-(3-hydroxy-2-(methoxycarbonyl)phenoxy)propyl)phenyl)isoxazole-3-carboxylic acid;

5-(2-fluoro-5-((1E)-3-(3-hydroxy-2-(methoxycarbonyl)phenoxy)prop-1-enyl)phenyl)isoxazole-3-carboxylic acid;

5-(3-((1E)-3-(3-hydroxy-2-nitrophenoxy)prop-1-enyl)phenyl)isoxazole-3-carboxylic acid;

5-{3'-(3-(carboxy)isoxazol-5-yl)-1,1'-biphenyl-3-yl}isoxazole-3-carboxylic acid;

5-(3-((1S,2S)-2-((3-hydroxy-2-(methoxycarbonyl)phenoxy)methyl)cyclopropyl)phenyl)isoxazole-3-carboxylic acid;

5-(3-(3-(3-hydroxy-2-(methoxycarbonyl)phenoxy)butyl)-4-methoxyphenyl)isoxazole-3-carboxylic acid;

5-(4-fluoro-3-(3-(3-hydroxy-2-(methoxycarbonyl)phenoxy)butyl)phenyl)isoxazole-3-carboxylic acid;

5-(3-(3-(3-hydroxy-2-(methoxycarbonyl)phenoxy)pentyl)phenyl)isoxazole-3-carboxylic acid;

5-(3-((1E)-3-(3-hydroxy-2-propionylphenoxy)prop-1-enyl)phenyl)isoxazole-3-carboxylic acid;

5-(3-((1E)-4-hydroxy-3-(3-hydroxy-2-(methoxycarbonyl)phenoxy)but-1-enyl)phenyl)isoxazole-3-carboxylic acid;

5-(1-(2-(3-hydroxy-2-(methoxycarbonyl)phenoxy)ethyl)-1H-indol-6-yl)isoxazole-3-carboxylic acid;

5-(3-((1E)-3-(2-(acetylamino)-3-hydroxyphenoxy)prop-1-enyl)phenyl)isoxazole-3-carboxylic acid;

5-(3-((1E)-3-(2-((benzylamino)carbonyl)-3-hydroxyphenoxy)prop-1-enyl)phenyl)isoxazole-3-carboxylic acid;

5-(3-((1E)-3-(3-hydroxy-2-(methoxycarbonyl)-4-nitrophenoxy)prop-1-enyl)phenyl)isoxazole-3-carboxylic acid;

4-amino-5-(3-((1E)-3-(3-hydroxy-2-(methoxycarbonyl)phenoxy)prop-1-enyl)phenyl)isoxazole-3-carboxylic acid;

5-(3-((1E)-3-((3',5-dihydroxy-4-(methoxycarbonyl)-1,1'-biphenyl-3-yl)oxy)prop-1-enyl)phenyl)isoxazole-3-carboxylic acid; and 5-(3-{(1E)-3-(3-hydroxy-2-(methoxycarbonyl)phenoxy)prop-1-enyl}phenyl)-4-(hydroxymethyl)isoxazole-3-carboxylic acid.

According to another embodiment, the present invention is directed to a pharmaceutical composition comprising a therapeutically effective amount of a compound of formula (I–II) in combination with a pharmaceutically suitable carrier.

According to another embodiment, the present invention is directed to method of selectively inhibiting protein tyrosine phosphatase 1B comprising administering a therapeutically effective amount of a compound of formula (I–II) in combination with a pharmaceutically suitable carrier.

According to another embodiment, the present invention is directed to a method of treating disorders caused by overexpressed or altered protein tyrosine phosphatase 1B comprising administering a therapeutically effective amount of a compound of formula (I–II) in combination with a pharmaceutically suitable carrier.

According to another embodiment, the present invention is directed to a method of treating type I and type II diabetes, impaired glucose tolerance and insulin resistance, comprising administering a therapeutically effective amount of a compound of formula (I–II) in combination with a pharmaceutically suitable carrier.

According to another embodiment, the present invention is directed to a method of treating obesity comprising administering a therapeutically effective amount of a compound of formula (I–II) in combination with a pharmaceutically suitable carrier.

According to another embodiment, the present invention is directed to a method of treating autoimmune disorders, acute and chronic inflammatory disorders, osteoporosis, cancer, malignant disorders comprising administering a therapeutically effective amount of a compound of formula (I–II) in combination with a pharmaceutically suitable carrier.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds can also be quatemized with alkyl chlorides, bromides, and iodides such as methyl, ethyl, propyl, isopropyl, butyl, lauryl, myristyl, stearyl, and the like.

Basic addition salts can be prepared during the final isolation and purification of the compounds by reacting an acidic group (for example, a carboxy group or an enol) with a suitable base such as the hydroxide, carbonate, or bicarbonate of a metal cation or with ammonia or an organic primary, secondary, or tertiary amine. The cations of pharmaceutically suitable salts include lithium, sodium, potassium, calcium, magnesium, and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of basic addition salts include ethylenediamine, ethanolamine, diethanolamine, piperidine, and piperazine.

Preferred salts of the compounds of the present invention include sodium and hydrochloride.

The present compounds can also exist as therapeutically suitable prodrugs. The term "therapeutically suitable prodrug," refers to those prodrugs which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I–II) for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients or carriers The term "therapeutically suitable excipient or carriers," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of PTP-1B by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer, and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I–II) to effectively ameliorate disorders by inhibiting PTP-1B at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. Single dose compositions can contain such amounts or submultiples thereof of the compounds to make up the daily dose. In general, treatment regimens comprise administration to a patient in need of such treatment from about 10 mg to about 1000 mg of the compounds per day in single or multiple doses. Single dose compositions can contain such amounts or multiple doses thereof of the compounds of the present invention to make up the daily dose. In general, treatment regimens comprise administration to a patient in need of such treatment from about 10 mg to about 1000 mg of the compounds per day in single or multiple doses.

The present invention may be illustrated by the use of the following non-limiting information:

Biological Data

A panel of different phosphatases is selected for assaying the different inhibitory activities exhibited by the claimed compounds. These phosphatases are selected on the basis of their homology to PTP1B, from the most homologous one, such as TCPTP, the moderate homologous phosphatase, such as SHP-2 and LAR, to the least homologous ones, such as cdc25c, CD45 and PP2B.

Purification of Human Protein Tyrosine Phosphatase 1B from *E. coli*.

Human protein tyrosine phosphatase 1B (PTP1B, amino acid residues 1–321) was expressed in *E. coli* BL21(DE3). The cell paste was resuspended in 4 cell paste volumes of lysis buffer containing 100 mM MES (pH 6.5), 100 mM NaCl, 1 mM EDTA, 1 mM DTT, 1 mM PMSF, 20 U/mL Benzonase, 0.5 mg/mL lysozyme, and 1 mM $MgCl_2$ and incubated for 35 minutes at room temperature. The cells were lysed at 11,000 psi using a Rannie homogenizer, and the homogenate was clarified in a Beckman GSA rotor at 10,000×g for 30 minutes at 4° C. The supernatant was loaded onto a 5×21 cm S-Sepharose-FF column (Amersham Pharmacia Biotech) pre-equilibrated with 5 column volumes of buffer containing 100 mM MES (pH 6.5), 100 mM NaCl, 1 mM EDTA, and 1 mM DTT. After sample application, the column was washed with 10 column volume (CV) of the same buffer, PTP1B was eluted with a 20 CV linear gradient of 100 mM to 500 mM NaCl in the same buffer. The fractions (28 mL each) were assayed for purity by 10–20% Tris-Glycine SDS-PAGE. Fractions which contained>95% protein tyrosine phosphatase 1B were combined. These fractions were concentrated to approximately 10 mg/mL by ultrafiltration and chromatographed on a 180 mL (1.6 cm×90 cm) Superdex 75 column in 10 mM TRIS-HCl, pH 7.5, 25 mM NaCl, 0.2 mM EDTA, 3 mM DTT. The fractions (2 mL each) were assayed for purity by 10–20% Tris-Glycine SDS-PAGE. Fractions which contained>99% protein tyrosine phosphatase 1B were combined. Aliquots were frozen in liquid $N_2$ and stored at $-70°$ C. until used. Once thawed, PTP1B was stored on ice and used within 6 hours.

Inhibition Constant Determination for Protein Tyrosine Phosphatase 1B:

Protein tyrosine phosphatase 1B activity was determined by measuring the rate of hydrolysis of a surrogate substrate, p-nitrophenyl phosphate (aka pNPP, C1907 Sigma, St. Louis, Mo.). The assay was carried out at room temperature in 96 well polypropylene or polyethylene plates in a total volume of 100 μL per well. Appropriate dilutions of the compounds were made in DMSO and then diluted by ten fold with water. 10 μL of 5 concentrations of the test compound (inhibitor) or 10% DMSO in water were added to individual wells containing 40 μL of 3.2, 8, 20, and 50 mM pNPP in water. The reaction was initiated by adding 50 μL of diluted PTP1B diluted in 2× assay buffer containing 50 mM HEPES (pH 7.5), 300 mM NaCl and 0.2 mg/mL BSA. The phosphatase activity results in the formation of the colored product p-nitrophenol (pNP) which was continuously monitored at 405 nm every 30 seconds for 15 minutes using an appropriate plate reader. The absorbance at 405 nm was converted to nanomoles of pNP using a standard curve and the initial rate of pNP formation was calculated. For each concentration of test compound (inhibitor) or DMSO control, the initial rates are used to fit the rectangular hyperbola of Michaelis-Menten by non-linear regression analysis (GraphPad Software Prism 3.0). The ratio of the apparent Km/Vmax vs. inhibitor concentration was plotted and the competitive Ki was calculated by linear regression to be the negative x-intercept. The uncompetitve Ki was similarly calculated from the x-intercept of the plot of the reciprocal of the apparent Vmax versus the inhibitor concentration. (Cornish-Bowden , A. 1995. Fundamentals of Enzyme Kinetics. Revised edition. Portland Press, Ltd., London, U.K.).

Sources of Other Phosphates Used in the Selectivity Panel:

TCPTP used was either obtained commercially (catalog #752L New England Biolabs, 32 Tozer $R_d$, Beverly, Mass.) or as described for PTP1B. The purification of TCPTP differed from the purification of PTP1b in that chromatography of TCPTP (amino acid residues 1–283) was on Q-Sepharose-FF (Amersham Pharmacia Biotech) in 50 mM TRIS-HCl; pH 7.5, 2 mM DTT, 10% (v/v) glycerol, and was eluted with a 3CV gradient of 0–300 mM NaCl in the same buffer. Fractions which contained TCPTP were selected and pooled based on SDS-PAGE. They were dialyzed versus 40 mM sodium phosphate, pH 7.5, 1 M ammonium sulfate, 10% (v/v) glycerol, 2 mM DTT, 1 mM sodium azide, applied to Phenyl Sepharose FF (Amersham Pharmacia Biotech), washed with 2.5 CV of the same buffer, and eluted with a 7 CV gradient of 1M to 0M NaCl in the same buffer. Fractions were assayed, pooled, frozen and stored as described for PTP1B.

SHP-2 (full length) was expressed in from *E. coli* and was purified as described for PTP-1B. Cells were lysed with a French press following by centrifugation to remove debris. Proteins were precipitated with 50% saturated ammonium sulfate, recovered by centrifugation, and chromatographed on Sephadex G-25 (Amersham Pharmacia Biotech) in 50 mM Tris-HCl pH 8, 10 mM NaCl, 1 mM DTT, 1 mM EDTA. The void volume was pooled and chromatographed on Q-Sepharose-FF in the same buffer, and SHP-2 was eluted with a 0–150 mM gradient of NaCl in the same buffer. Fractions were assayed, pooled, and stored as described for PTP1B.

CDC25c was expressed as a fusion with glutathione-S-transferase (aka GST) in *E. coli*. Cells were lysed and debris removed as described for SHP-2, except lysis was in PBS (GibcoBRL Life Technologies, Grand Island, N.Y., Stock # 70011-044, diluted 10-fold). The soluble proteins were chromatographed on Glutathione-Sepharose FF (Amersham Pharmacia Biotech) and eluted with 10 mM reduced glutathione in 25 mM TRIS-HCl, pH 7.5, 150 mM NaCl. Fractions were assayed, pooled and stored as described for PTP1B.

CD45 was obtained commercially (catalog #SE-135 Biomol Research Laboratories, Inc. 5120 Butler Pike, Plymouth Meeting, Pa.).

LAR was obtained commercially (catalog #P0750L New England Biolabs, 32 Tozer Rd, Beverly, Mass.).

Bovine PP2B was obtained commercially (C1907 Sigma, St. Louis, Mo.).

Inhibition Constant Determination for Other Phosphatases in the Selectivity Panel:

The $K_{ic}$ and $K_{iu}$ values are calculated as described for PTP1B. The assays were performed as described for PTP-1B except for the following changes. All the phosphatases except PP2B use the same 2× assay buffer as PTP1B. PP2B uses a 2× assay buffer which contains 100 mM TRIS-HCl pH 8.6, 40 mM $MgCl_2$, 0.2 mM $CaCl_2$, 6 mM DTT, 0.2 mg/mL BSA. The concentrations of pNPP present in 40 ul were the same for TCPTP, CD45, LAR and PTP1B. For PP2B they were 24 mM, 60 mM, 150 mM, and 375 mM; for cdc25C they were 16 mM, 40 mM, 100 mM, and 250 mM; for SHP-2 they were 6.4 mM, 16 mM, 40 mM, and 100 mM.

TABLE 1

| | Phosphatase Inhibition Constants ($K_{ic}$) | | | | | | |
|---|---|---|---|---|---|---|---|
| Compound of Example # | PTP1B | TC-PTP | SHP-2 | LAR | CD45 | PP2B | Cdc25c |
| 1 | 5.7 +/− 0.9 | 201.6 +/− 26.5 | >300 | >300 | >300 | >300 | >300 |
| 8 | 6.9 +/− 2.3 | 164 +/− 1.0 | >300 | >300 | >300 | >300 | >300 |

($K_{ic}$ expressed in μM +/− S.D.)

The results shown in Table 1 demonstrate that compounds of Example 1 and 8 are at least 20 fold selective for PTP1B over the most homologous phosphatase, TCPTP, are over 40 fold selective for PTP1B over SHP-2, LAR, CD45, PP2B and Cdc25C. Moreover, the compounds of the present invention were found to inhibit protein tyrosine phosphatase 1B with inhibitory constants in a range of about 0.1 μM to about 100 μM. In a preferred range, the compounds inhibited protein tyrosine phosphatase 1B with inhibitory constants in a range of about of about 0.1 µM to about 10 µM.

Synthetic Methods

The compounds and processes of the present invention will be better understood in connection with the following synthetic non-limiting schemes which together illustrate the methods by which the compounds of the invention may be prepared. Starting materials can be obtained from commercial sources or prepared by well-established literature methods known to those of ordinary skill in the art. The synthesis of compounds of formula (I–II), wherein the groups R, $R_1$, $R_2$, $R_3$, $R_4$, $R_5$, $R_6$, $R_7$, L, G, J, K, $X_1$, $X_2$, $R_a$, $R_b$, $R_c$, $R_d$, $R_e$ are as defined above unless otherwise noted below, are exemplified below.

Scheme 1

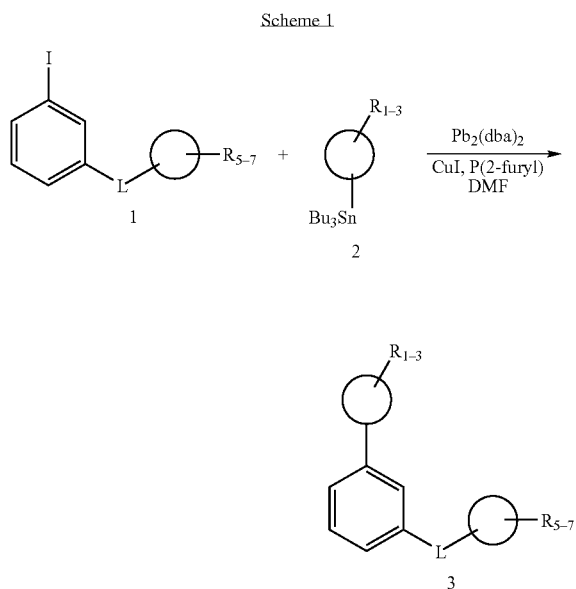

As shown in Scheme 1, compounds of formula 1 can be reacted with organometallic reagents of formula 2 using a palladium catalyst such as $Pb_2(dba)_2$ (tris(dibenzylideneacetone)-dipalladium(0)), $P(2-furyl)_3$ (tri-2-furylphosphine), copper iodide in solvents such as but not limited to DMF to provide compounds of formula 3 which are representative of compounds of formula (I).

Scheme 2

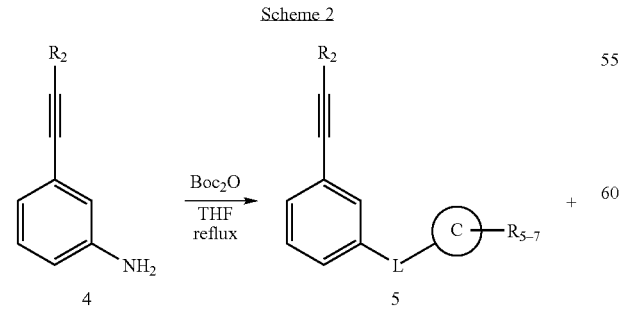

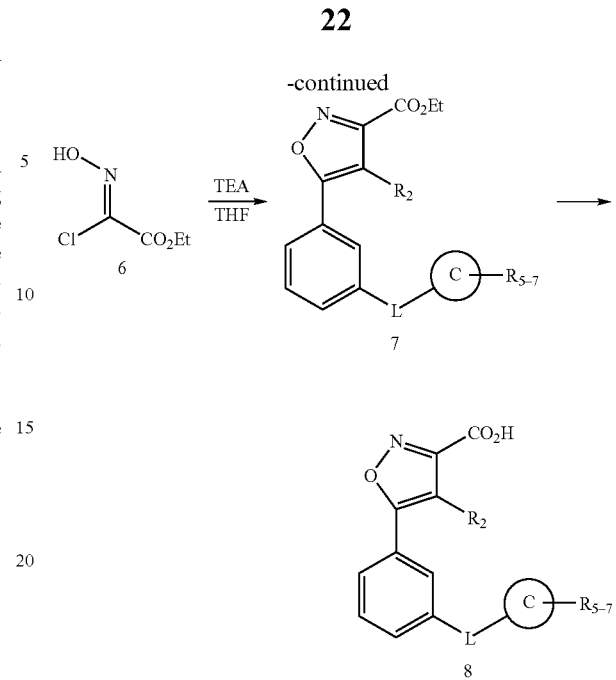

As shown in Scheme 2, compounds of formula 4 can be protected with nitrogen protecting groups known in the art such as but not limited to BOC (tert-butyloxycarbonyl) to provide compounds of formula 5 or others suitable for use in further synthetic pathways. Compounds of formula 5 can be treated with compounds of formula 6 and a base such as triethylamine in solvents such as but not limited to THF to provide compounds of formula 7 which are representative of compounds of formula (I) when $R_1$ is alkoxycarbonyl, and $R_2$ is alkyl, aryl, arylalkyl, cycloalkylalkyl, heterocycle or heterocyclealkyl. Compounds of formula 7 can be treated with reagents known to those skilled in the art to hydrolyze alkoxycarbonyl group to their corresponding carboxy groups for example sodium hydroxide or lithium hydroxide in aqueous alcoholic solutions or aqueous THF to provide compounds of formula 8 which are representative of compounds of formula (I–II) when $R_1$ is carboxy.

Scheme 3

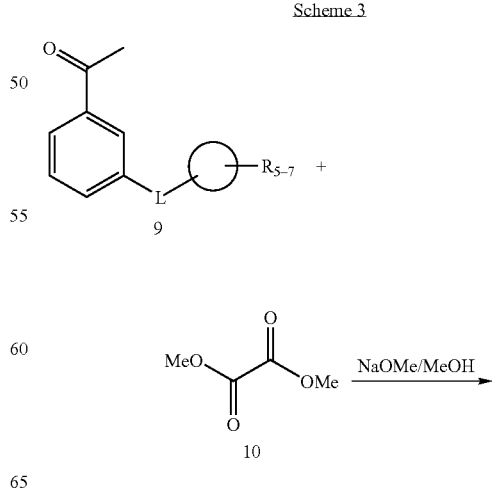

-continued

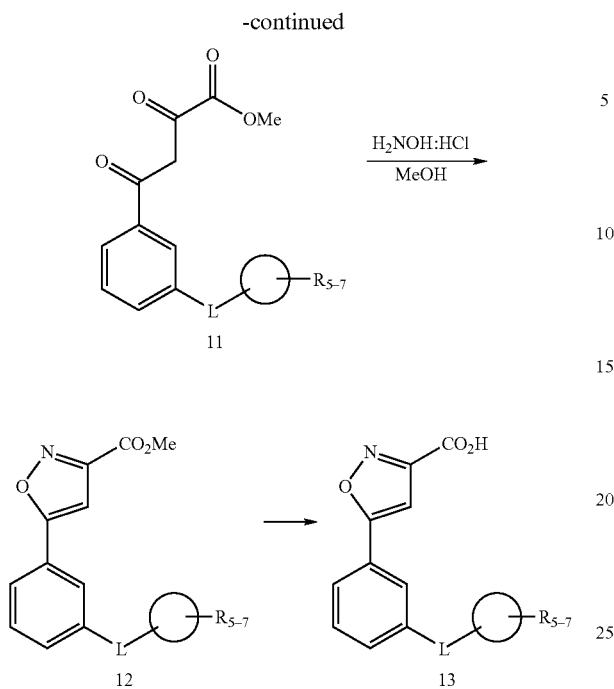

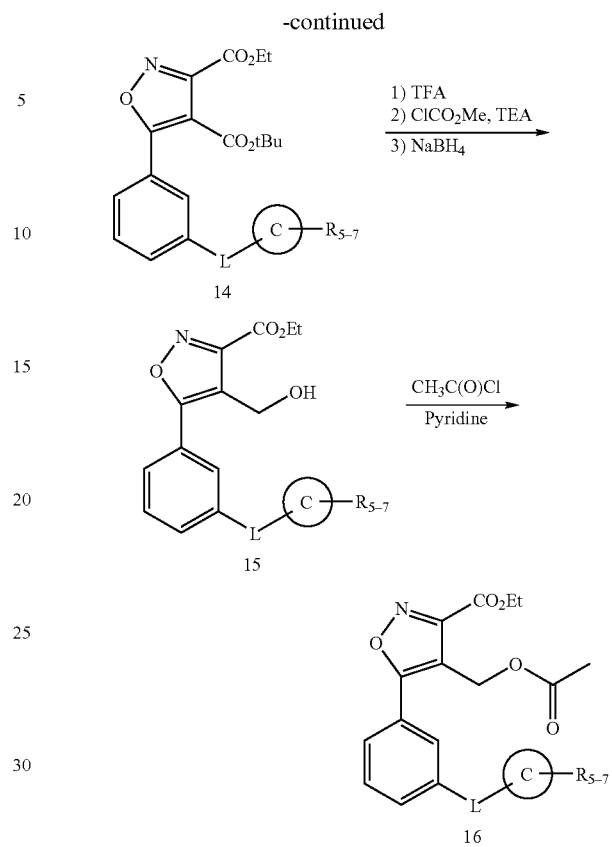

As shown in Scheme 3, compounds of formula 9 may be treated with compounds of formula 10 and sodium methoxide in methanol to provide compounds of formula 11. Compounds of formula 11 may be treated with hydroxylamine hydrochloride in methanol to provide compounds of formula 12 which are representative of compounds of formula (I–II) where $R_1$ is alkoxycarbonyl. Compounds of formula 12 can be treated according to conditions described in Scheme 2 to hydrolyze the alkoxycarbonyl functionality to provide compounds of formula 13 which are also representative of compounds of formula (I–II) where $R_1$ is carboxy.

As shown in Scheme 4, compounds of formula 11 can be reacted with compounds of formula 6 and TEA in solvents such as but not limited to THF to provide compounds of formula 14. Compounds of formula 14 when treated with TFA in dichloromethane will selectively deprotect the t-butyl ester to provide the corresponding carboxy group at the $R_2$ position. The carboxy group may then be treated with methyl chloroformate and TEA to provide the corresponding anhydride which upon treatment with sodium borohydride provides compounds of formula 15. The primary alcohol portion of compounds of formula 15 may be further functionalized using conditions known to those skilled in the art such as treatment with acetyl chloride and pyridine to provide compounds of formula 16 which are representative of compounds of formula (I–II).

Scheme 4

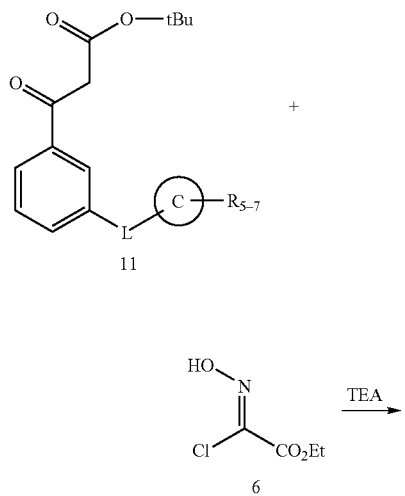

Scheme 5

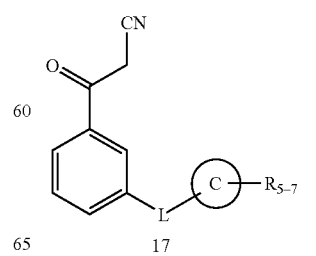

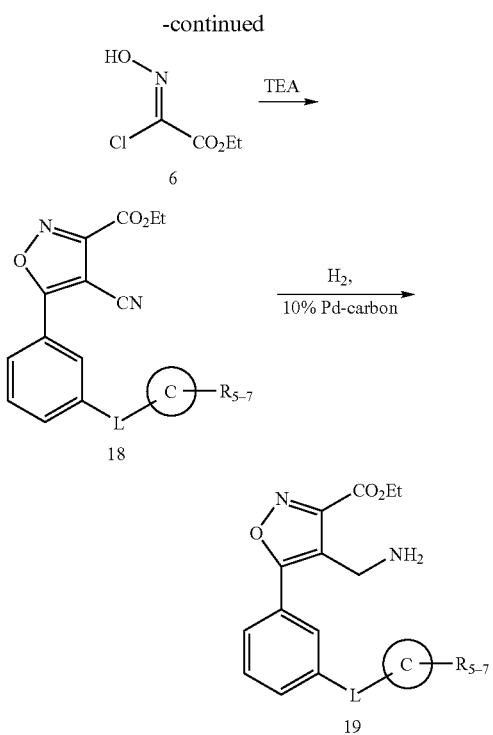

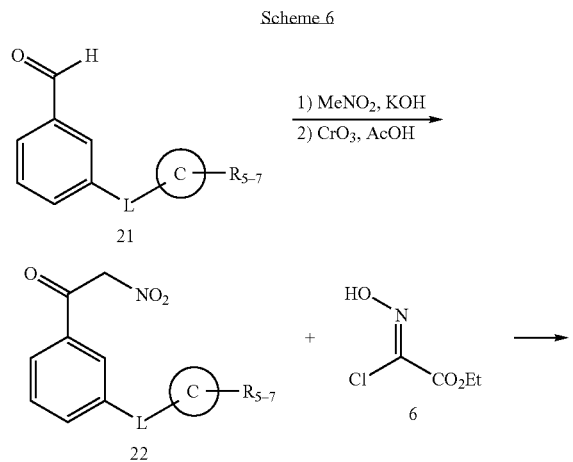

As shown in Scheme 5, compounds of formula 17 may also be reacted with compounds of formula 6 and triethylamine to provide compounds of formula 18 which are representative of compounds of formula (I–II). The nitrile portion of compounds of formula 18 may be further treated with palladium on carbon in a pressurized atmosphere of hydrogen in solvents such as but not limited to ethanol to provide compounds of formula 19 which are representative of compounds of formula (I–II) where $R_2$ is $NH_2$alkyl. The $NH_2$ portion of compounds of formula 19 may be further treated with reagents known to react with amines to further functionalize the amine portion to provide compounds of formula (I–II) where $R_2$ is a member selected from the group consisting of $R_aR_bN$—.

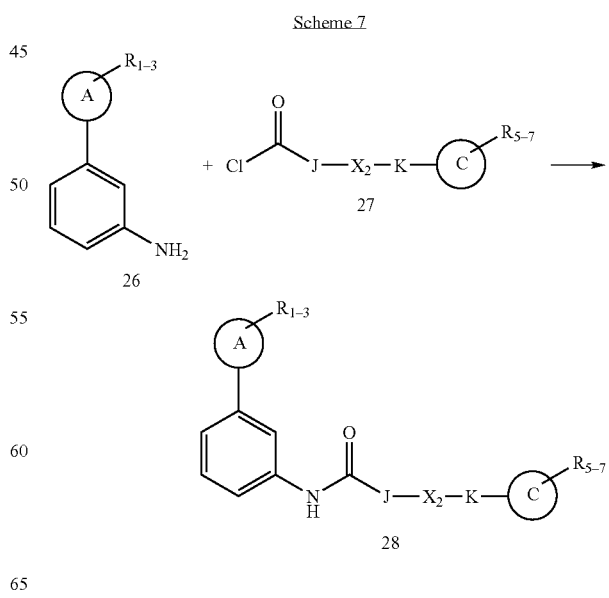

As shown in Scheme 6, compounds of formula 21 may be treated with nitromethane and potassium hydroxide followed by treatment with chromium dioxide in acetic acid to provide compounds of formula 22. Compounds of formula 22 can be treated with compounds of formula 6 and TEA in solvents such as but not limited to THF to provide compounds of formula 23 which are representative of compounds of formula (I–II) where $R_1$ is alkoxycarbonyl and $R_2$ are nitro. The nitro portion of compounds of formula 23 can be reduced using conditions known to those skilled in the art to provide compounds of formula 24. Furthermore, the alkoxylcarbonyl portion of compounds of formula 23 or 24 may be hydrolyzed using conditions set forth in Scheme 2 to provide the carboxy analog of a compound of formula 23 or to provide a compound of formula 25 when hydrolyzing a compound of formula 24, both of which are representative of compounds of formula (I–II).

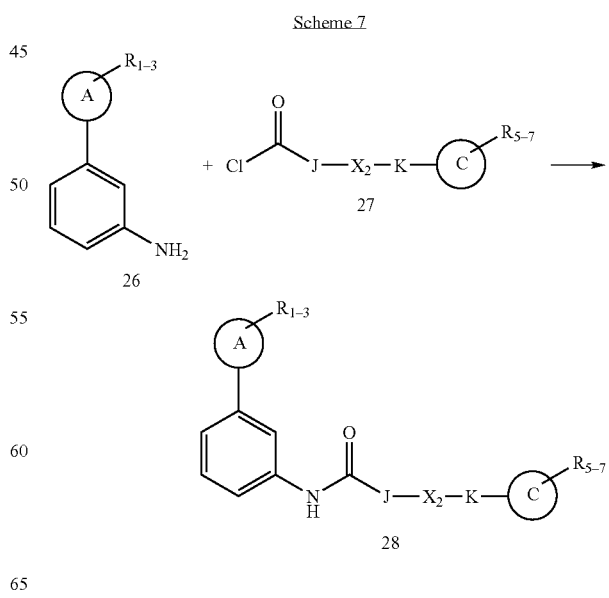

As shown in Scheme 7, compounds of formula 26 may be treated with the acid chloride portion of compounds of formula 27 in the presence of a base such as but not limited to triethylamine, N-methylmorpholine and the like in solvents such as but not limited to dichloromethane to provide compounds of formula 28 which are representative of compounds of formula (I).

Scheme 8

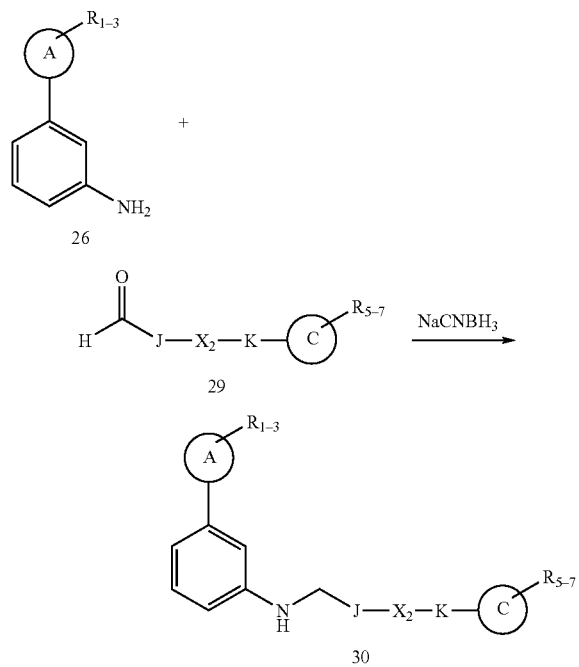

As shown in Scheme 8, compounds of formula 26 may be reacted with compounds of formula 29 and sodium cyanoborohydride in solvents such as but not limited to ethanol or THF to provide compounds of formula 30 which are representative of compounds of formula (I).

Scheme 9

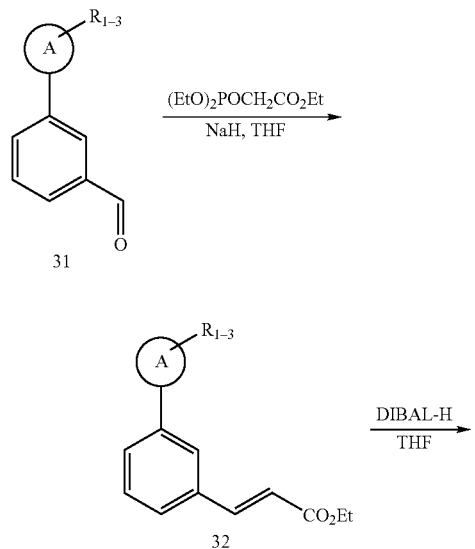

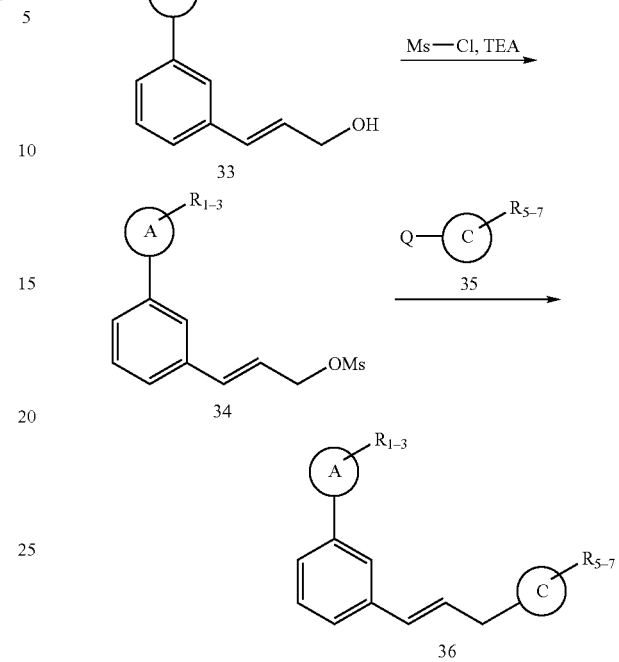

As shown in Scheme 9, compounds of formula 31 may be reacted with Horner-Emmons reagents or conditions known to those skilled in the art to homologate aldehydes to provide compounds of formula 32. Compounds of formula 32 may be treated with DIBAL-H in THF to provide compounds of formula 33. The alcohol portion of compounds of formula 33 may be treated with methanesulfonyl chloride and triethylamine in dichloromethane to provide compounds of formula 34. Compounds of formula 34 may be treated with compounds of formula 35 (wherein Q is a metal selected from the group consisting of sodium, lithium, potassium, magnesium bromide) to provide compounds of formula 36 which are representative of compounds of formula (I).

Scheme 10

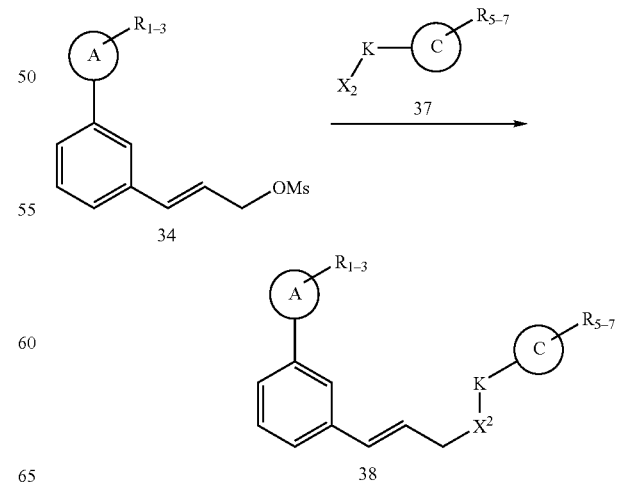

Similarly, as shown in Scheme 10, compounds of formula 34 can be treated with compounds of formula 37 (where $X_2$ is hydroxy, or $NH(R_c)$—, K is alkyl or alkenyl) to provide compounds of formula 38 which are representative of compounds of formula (I). When $X_2$ is hydroxy, sodium hydride in DMF is required and when $X_2$ is $NH(R_c)$— acetonitrile and heating conditions are often required.

Scheme 11

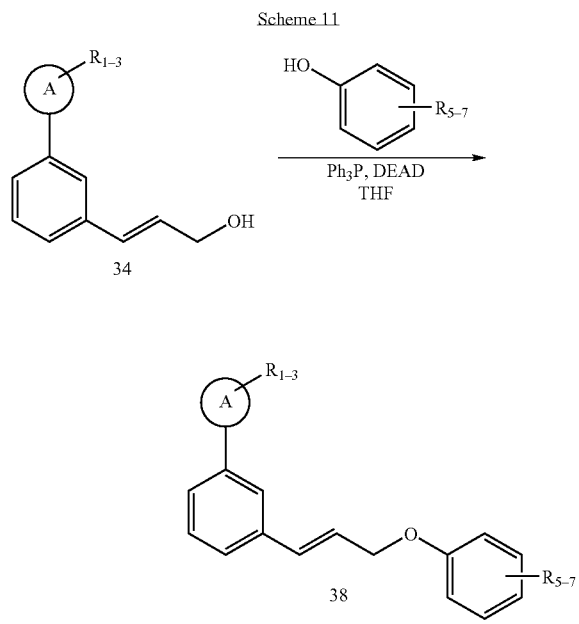

Alternatively, compounds of formula 34 may be reacted with substituted phenols, triphenyphosphine and diethyl azodicarboxylate in THF or by similar conditions known to those skilled in the art to provide compounds of formula 38 which are representative of compounds of formula (I).

Scheme 12

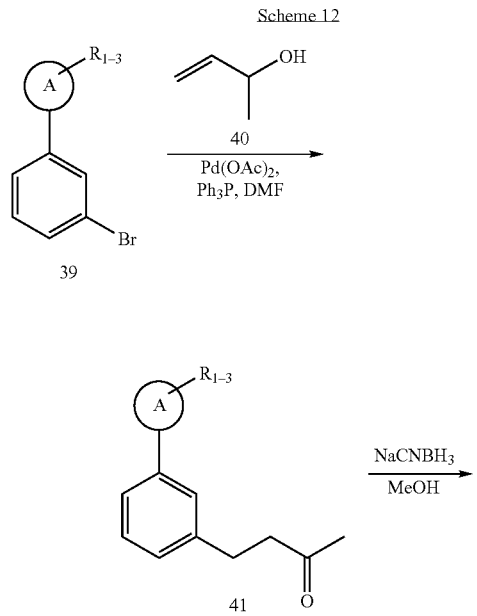

-continued

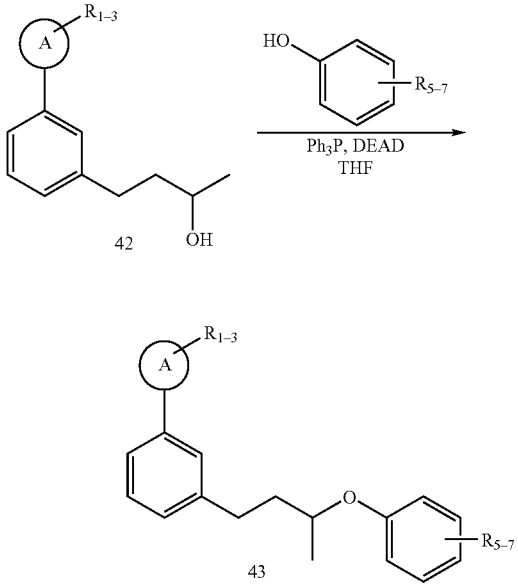

As shown in Scheme 12, compounds of formula 39 can be treated with allylic alcohols such as but not limited to compounds of formula 40, palladium acetate, triphenylphosphine in DMF to provide compounds of formula 41. Compounds of formula 41 can be treated with sodium cyanoborohydride in methanol to provide compounds of formula 42. The alcohol portion of the compound of formula 42 can be treated with phenols, triphenylphosphine and diethyl azodicarboxylate in THF or by conditions known to those skilled in the art to create compounds of formula 43 which are representative of compounds of formula (I).

Scheme 13

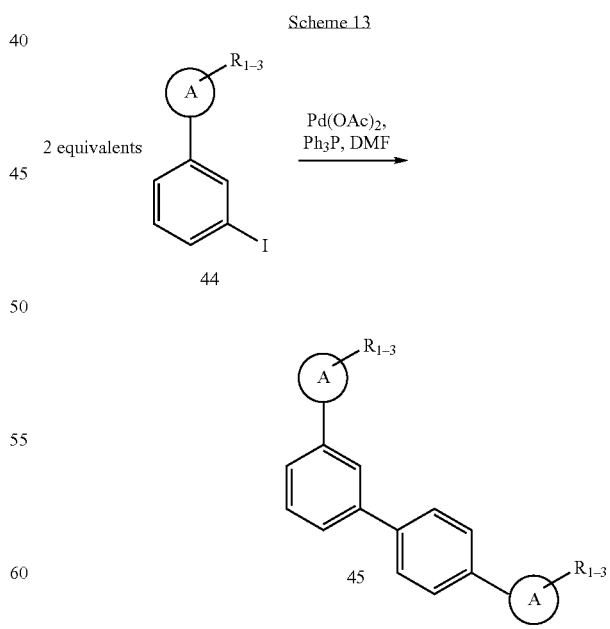

As shown in Scheme 13, 2 equivalents of a compounds of formula 44 can be treated with palladium acetate, triphenylphosphine in DMF to provide a compounds of formula 45 which is representative of compounds of formula (I).

Scheme 14

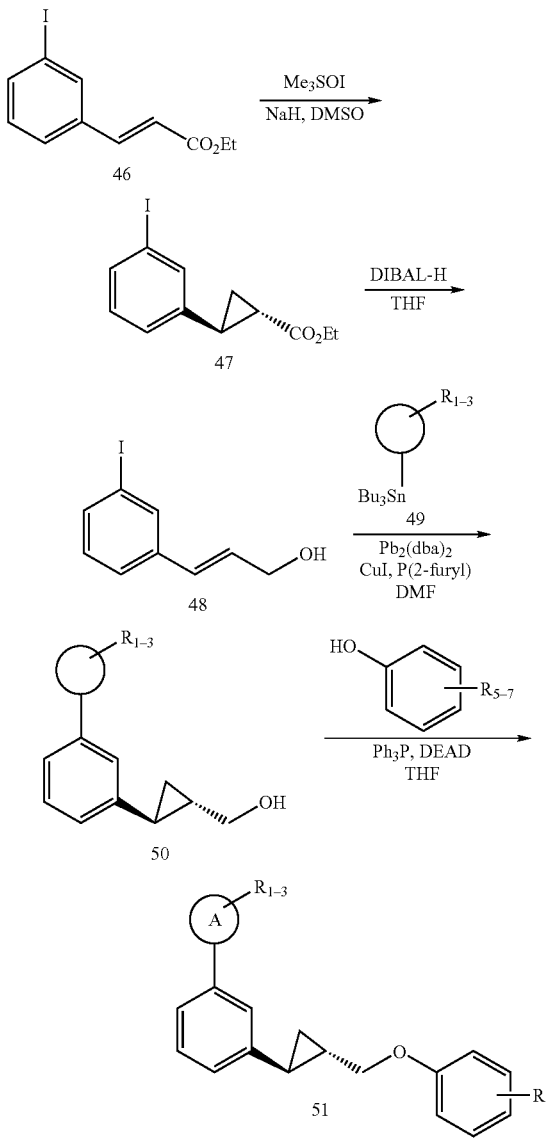

As shown in Scheme 14, compounds of formula 46 can be treated with trimethylsulfoxonium iodide, sodium hydride in DMSO to provide compounds of formula 47. Compounds of formula 47 can be treated with DIBAL-H in THF to provide compounds of formula 48. Compounds of formula 48 can be treated with reagents outlined in Scheme 1 to provide compounds of formula 50. Compounds of formula 50 can be treated under conditions outlined in Scheme 11 and 12 to provide compounds of formula 51.

The compounds and processes of the present invention will be better understood by reference to the following examples, which are intended as an illustration of and not a limitation upon the scope of the invention.

Compounds of the invention were named by ACD/Chem-Sketch version 5.01 (developed by Advanced Chemistry Development, Inc., Toronto, ON, Canada) or were given names consistent with ACD nomenclature.

EXPERIMENTALS

Example 1

5-(3-((1E)-3-(3-hydroxy-2-(methoxycarbonyl)phenoxy)prop-1-enyl)phenyl)isoxazole-3-carboxylic acid

Example 1A ethyl (2E)-3-(3-iodophenyl)acrylate

To a suspension of NaH (60% dispersion in mineral oil) (120 mg, 3.0 mmol) in THF (20 mL) was added triethyl phosphonoacetate (436 μL, 2.2 mmol) dropwise. 3-iodobenzaldehyde (465 mg, 2.0 mmol) was added after the bubbling has stopped. The reaction mixture was stirred at room temperature for 15 minutes. Solid NH$_4$Cl was added, followed by 1N HCl to quench the reaction. The mixture was taken up in ethyl acetate and water. The organic phase was washed with aqueous NaHCO$_3$, brine, dried (MgSO$_4$), filtered and concentrated under reduced pressure and purified by flash chromatography on silica gel with hexane/ethyl acetate (4:1) to provide the titled compound (605 mg).

Example 1B (2E)-3-(3-iodophenyl)prop-2-en-1-ol

The material from Example 1A (2.0 mmol) was dissolved in THF (10 mL). DIBAL-H (1 M in hexane, 6 mL, 6.0 mmol) was added. The reaction mixture was stirred at ambient temperature for 30 minutes. Saturated sodium potassium tartrate solution was added slowly at 0° C., followed by addition of diethyl ether. The mixture was stirred vigorously overnight. The organic phase was separated and washed with brine, dried (MgSO$_4$), filtered and concentrated under reduced pressure to provide titled compound (489 mg). MS (ESI(−)) m/e 259 (M−H)$^+$; $^1$H NMR (300 MHz, DMSO-d$_6$) δ 7.79(t, J=1.7 Hz, 1H), 7.57 (dt, J$_1$=1.7 Hz, J$_2$=7.8 Hz, 1H), 7.45 (dt, J$_1$=1.7 Hz, J$_2$=7.8 Hz, 1H), 7.12 (t, J=7.8 Hz, 1H), 6.48–6.42 (m, 2H), 4.89 (t, J=5.8 Hz, 1H), 4.11 (m, 2H).

Example 1C ethyl 5-(tert-butylstannyl)isoxazole-3-carboxylate

Triethylamine (3.84 mL, 27.4 mmol) was added to a solution of tributyltin acetylene (5.4 g, 17.1 mmol) and ethyl chlorooximidoacetate (3.89 g, 25.7 mmol) in diethyl ether (100 mL). The reaction mixture was stirred at ambient temperature for 30 minutes, and filtered through celite. The filtrate was concentrated under reduced pressure and purified by flash chromatography on silica gel with hexane/ethyl acetate (8:1) to provide the titled compound (6.9 g). $^1$H NMR (300 MHz, DMSO-d$_6$) δ 6.91 (s, 1H), 4.35 (q, J=7.1 Hz, 2H), 1.68–1.08 (m, 9H), 0.85 (t, J=7.1 Hz, 3H).

Example 1D ethyl 5-(3-((1E)-3-hydroxyprop-1-enyl)phenyl)isoxazole-3-carboxylate The tributyltin reagent from Example 1C (665 μL, 1.83 mmol) was added under nitrogen atmosphere to a mixture of alcohol from Example 1B (433 mg, 1.66 mmol), tris(dibenzylideneacetone)-dipalladium(0) (76 mg, 0.083 mmol), tri-2-furylphosphine (39 mg, 0.166 mmol), and cupper(I) iodide (32 mg, 0.166 mmol) in DMF (7 mL). The reaction mixture was stirred at ambient temperature for 30 minutes. Aqueous potassium fluoride was added to the mixture and the resulting suspension was filtered through celite and washed with ethyl acetate. The filtrate was taken up in ethyl acetate and water. The organic phase was washed with brine (×3), dried ($MgSO_4$), filtered and concentrated under reduced pressure and purified by flash chromatography on silica gel with hexane/ethyl acetate (1:1) to provide the titled compound (353 mg). MS (ESI(+)) m/e 291 (M+18)$^+$; $^1$H NMR (500 MHz, DMSO-$d_6$) δ 8.05(t, J=1.7 Hz, 1H), 7.80 (dt, $J_1$=1.7 Hz, $J_2$=7.5 Hz, 1H), 7.60 (dt, $J_1$=1.7 Hz, $J_2$=7.5 Hz, 1H), 7.57 (s, 1H), 7.51(t, J=7.5 Hz, 1H), 6.63–6.59 (m, 2H), 4.94 (t, J=5.4 Hz, 1H), 4.41 (q, J=7.1 Hz, 2H), 4.19–4.14(m, 2H), 1.35 (t, J=7.1 Hz, 3H).

Example 1E ethyl 5-(3-((1E)-3-(3-hydroxy-2-(methoxycarbonyl)phenoxy)prop-1-enyl)phenyl)isoxazole-3-carboxylate To the mixture of Example 1D (96 mg, 0.35 mmol), 2,6-dihydroxy methyl benzoate (77 mg, 0.46 mmol), and triphenylphosphine (129 mg, 0.49 mmol) in THF (1.5 mL) was added diethylazodicarboxylate (77 μL, 0.49 mmol). The reaction mixture was stirred at ambient temperature for 30 minutes and then concentrated under reduced pressure. The concentrate was purified by flash chromatography on silica gel with hexane/ethyl acetate (3:1) to provide the titled compound (61 mg).

Example 1F 5-(3-((1E)-3-(3-hydroxy-2-(methoxycarbonyl)phenoxy)prop-1-enyl)phenyl)isoxazole-3-carboxylic acid To a solution of Example 1E in THF/MeOH (1:1 10 mL), was added 2N NaOH (225 μL, 0.45 mmol). The reaction mixture was stirred at ambient temperature for 10 minutes and quenched with 1N HCl and extracted with ethyl acetate. The organic phase was washed with water, dried ($MgSO_4$), filtered and concentrated to provide the titled compound. MS (ESI(+)) m/e 413 (M+18)$^+$; $^1$H NMR (300 MHz, DMSO-$d_6$) δ 9.96 (s, 1H), 8.06(s, 1H), 7.83(d, J=7.5 Hz, 1H), 7.61 (d, J=7.8 Hz, 1H), 7.53 (t, J=7.5 Hz, 1H), 7.49(s, 1H), 7.19(t, J=8.4 Hz, 1H), 6.79 (d, J=15.9 Hz, 1H), 6.65 (dt, $J_1$=15.9 Hz, $J_2$=5.8 Hz, 1H), 6.61(d, J=8.4 Hz, 1H), 6.52(d, J=8.4 Hz, 1H), 4.75(d, J=5.0 Hz, 2H), 3.79 (s, 3H).

Example 2

5-(3-(3-(3-hydroxy-2-(methoxycarbonyl)phenoxy)butyl)phenyl)isoxazole-3-carboxylic acid Example 2A methyl 4-(3-bromophenyl)-2,4-dioxobutanoate To a mixture of 3'-bromoaceptophone (8.0 g, 40.1 mmol) and dimethyl oxalate (7.2 g, 60.3 mmol) in anhydrous methanol (120 mL) was added 25% sodium methoxide/methanol solution (19.3 mL, 84.4 mmol) dropwise. The resulting mixture Was heated at 65° C. for 2 hours, the mixture was cooled to room temperature, poured into 1N HCl solution (200 mL). The light yellow precipitate was collected through filtration, washed with cold water, and dried in a vacuum oven to give the titled compound (10.4 g, 89% yield).

Example 2B 5-(3-Bromo-phenyl)-isoxazole-3-carboxylic acid methyl ester

To a suspension of 2,4-dioxo-4-(3-bromophenyl)-butyric acid methyl ester (10.3 g, 36.1 mmol) in anhydrous MeOH (100 mL) was added hydroxylamine hydrochloride (3.8 g, 54.2 mmol). The mixture was then refluxed for 90 min. The reaction mixture was then cooled to room temperature, and ice/water mixture (200 mL) was added. The mixture was stirred for 20 minutes, filtered through a Buchner funnel and washed with cold water. The light yellow solid was dried in vacuum oven to provide the title compound (8.9 g, 87% yield).

Example 2C 5-(3-(3-Oxo-butyl)-phenyl)-isoxazole-3-carboxylic acid methyl ester

To a mixture of 5-(3-Bromo-phenyl)-isoxazole-3-carboxylic acid methyl ester (1.5 g, 5.3 mmol), Pd(OAc)$_2$ (60 mg, 0.27 mmol), P(o-tolyl)$_3$ (162 mg, 0.53 mmol) in anhydrous N,N-dimethylformamide (15 mL) in a pressure tube was added 3-buten-2-ol (0.92 mL, 10.6 mmol) and triethylamine (1.1 mL, 7.95 mmol). The mixture was flushed with nitrogen for 3 minutes, capped and heated to 100° C. for 30 minutes. The reaction mixture was allowed to cool to ambient temperature, partitioned between ethyl acetate and water (75 mL, 1:1). The organic layer was washed with brine (2×25 mL), dried ($Na_2SO_4$), filtered, concentrated under reduced pressure and purified on a Silica Gel MPLC eluting with 20–40% ethyl acetate/hexanes to provide the titled compound as a light yellow solid (860 mg, 59%). MS (ESI(+)) m/e 274 (M+H)$^+$.

Example 2D methyl 5-(3-(3-hydroxybutyl)phenyl)isoxazole-3-carboxylate

To a mixture of 5-(3-(3-Oxo-butyl)-phenyl)-isoxazole-3-carboxylic acid methyl ester (860 mg, 3.15 mmol) in methanol (15 mL)at room temperature was added $NaBH_4$ (178 mg, 4.7 mmol) with stirring. After 30 min, the reaction mixture was partitioned between ethyl acetate and 3N HCl. The organic layer was washed with brine, dried over $Na_2SO_4$, filtered, evaporated in vacuo to provide the titled compound as a light brown oil (850 mg, 99% yield).

Example 2E methyl 5-(3-(3-(3-hydroxy-2-(methoxycarbonyl)phenoxy)butyl)phenyl)isoxazole-3-carboxylate The titled compound was prepared according to the procedure described in Example 1E, substituting methyl 5-(3-(3-hydroxybutyl)phenyl)isoxazole-3-carboxylate for the ethyl 5-(3-((1E)-3-hydroxyprop-1-enyl)phenyl)isoxazole-3-carboxylate.

Example 2F 5-(3-(3-(3-hydroxy-2-(methoxycarbonyl)phenoxy)butyl)phenyl)isoxazole-3-carboxylic acid This title compound was prepared according to the procedure described in Example 1F, substituting Example 2E for Example 1E. MS (ESI(+)) m/e 412 (M+H)$^+$; $^1$H NMR (300 MHz, DMSO-d$_6$) δ 7.64 (s, 1H), 7.62 (d, J=6.3 Hz, 1H), 7.38 (t, J=8.1 Hz, 1H), 7.24 (d, J=8.1 Hz, 1H), 7.09 (t, J=8.1 Hz, 1H), 6.88 (s, 1H), 6.44 (d, J=6.3 Hz, 1H), 6.42 (d, J=6.3 Hz, 1H), 4.32 (sextet, J=6.0 Hz, 1H), 3.77 (s, 3H), 2.61–2.83 (m, 2H), 1.77–1.99 (m, 2H), 1.25 (d, J=6.0 Hz, 3H).

Example 3

5-(3-((2-(3-hydroxy-2-(methoxycarbonyl)phenoxy)ethyl)amino)phenyl)isoxazole-3-carboxylic acid

Example 3A 2-((3-iodophenyl)amino)ethanol

A mixture of 3-iodoaniline (2.0 g, 9.1 mmol) and 2-bromoethanol (0.32 mL, 4.6 mmol) in a sealed tube was heated at 160° C. for 2 hours. Cooled to room temperature, sat. NaHCO$_3$ and water were added. The resulting mixture was extracted with ethyl acetate, the organic layer was washed with brine, dried, evaporated under reduced pressure. The crude product was purified on a ISCO MPLC to provide the titled compound as a light brown oil (770 mg, 38.6% yield). MS (ESI(+)) m/e 264 (M+H)$^+$.

Example 3B methyl 2-hydroxy-6-(2-((3-iodophenyl)amino)ethoxy)benzoate

The titled compound was prepared according to the procedure described in Example 1E, substituting the allyl alcohol from Example 1D for the alcohol from Example 3A.

Example 3C ethyl 5-(3-((2-(3-hydroxy-2-(methoxycarbonyl)phenoxy)ethyl)amino)phenyl)isoxazole-3-carboxylate The titled compound was prepared according to the procedure described in Example 1D, substituting the iodide from Example 1A for the iodide from Example 3B.

Example 3D 5-(3-((2-(3-hydroxy-2-(methoxycarbonyl)phenoxy)ethyl)amino)phenyl)isoxazole-3-carboxylic acid The titled compound was prepared according to the procedure described in Example 1F, substituting the ester from Example 1E for the ester from Example 3C. MS (ESI(+)) m/e 399 (M+H)$^+$; $^1$H NMR (300 MHz, DMSO-d$_6$) δ 9.96 (s, 1H), 7.30 (s, 1H), 7.25 (t, J=8.4 Hz, 1H), 7.18 (t, J=8.4 Hz, 1H), 7.08–7.14 (m, 2H), 6.78 (dt, J=6.9, 1.5 Hz, 1H), 6.55 (d, J=5.8 Hz, 1H), 6.51 (d, J=5.8 Hz, 1H), 4.12 (t, J=5.7 Hz, 2H), 3.70 (s, 3H), 3.6–3.3 (overlapping m, 2H).

Example 4

5-(3-(((1-acetylpiperidin-4-yl)carbonyl)amino)phenyl)isoxazole-3-carboxylic acid

Example 4A (3-ethynyl-phenyl)-carbamic acid tert-butyl ester

To 3-ethynyl-phenylamine (5.66 g, 0.0483 mole) in TBF (90 mL) was added Boc$_2$O (6.07 g, 0.0278 mole). The mixture was heated to reflux for 16 hours, cooled to ambient temperature, taken up in ethyl acetate (200 mL) and washed with aqueous 1N HCl (3×50 mL), saturated Na$_2$CO$_3$ and brine. The organic layer was dried over anhydrous Na$_2$SO$_4$, filtered, concentrated in vacuo and purified by flash chromatography (15% ethyl acetate/Hexane) to provide the titled compound (10.46 g).

Example 4B 5-(3-tert-butoxycarbonylamino-phenyl)-isoxazole-3-carboxylic acid ethyl ester (3-ethynyl-phenyl)-carbamic acid tert-butyl ester (2.48 g, 0.0114 mole) and ethyl chlorooximidoacetate (3.82 g, 0.0252 mole) were mixed in THF (12 mL) and triethylamine (3.98 mL, 0.0286 mole) was added slowly. The mixture was stirred for 16 hours and then diluted with ethyl acetate (100 mL) and aqueous 1N HCl (50 mL). The two layers were separated and the aqueous layer extracted with ethyl acetate (2×50 mL). The combined organics were dried over anhydrous Na$_2$SO$_4$, filtered, concentrated in vacuo and purified by flash chromatography (10–15% ethyl acetate/Hexane) to provide the titled compound (2.64 g, 50% yield).

Example 4C ethyl 5-(3-aminophenyl)isoxazole-3-carboxylate 5-(3-tert-butoxycarbonylamino-phenyl)-isoxazole-3-carboxylic acid ethyl ester (2.63 g, 0.00791 mole) in methylene chloride. (5 mL) was treated with trifluoroacetic acid (2.5 mL) at ambient temperature for 4 hours. The mixture was concentrated in vacuo to provide the titled compound (3.68 g).

Example 4D ethyl 5-(3-{((1-acetylpiperidin-4-yl)carbonyl)amino}phenyl)isoxazole-3-carboxylate To ethyl 5-(3-aminophenyl)isoxazole-3-carboxylate (0.224 mmole) and triethylamine (0.896 mmole) in methylenechloride (3 mL) was added 1-acetyl-piperidine-4-carbonyl chloride HCl salt (0.314 mmole) via syringe at ambient temperature. After two hours, 1N HCl was added and the mixture was extracted with methylene chloride (3×40 mL). The combined organics were washed with aqueous Na$_2$CO$_3$, dried with anhydrous Na$_2$SO$_4$, filtered, concentrated under vacuo and purified by flash chromatography (10–15% ethyl acetate/Hexane) to provide (68 mg) of the titled compound.

Example 4E

5-(3-(((1-acetylpiperidin-4-yl)carbonyl)amino)phenyl)isoxazole-3-carboxylic acid Ethyl 5-(3-{((1-acetylpiperidin-4-yl)carbonyl)amino}phenyl)isoxazole-3-carboxylate (68 g) was dissolved in THF (1.2 mL) and treated with 1N NaOH solution (1 mL) at ambient temperature for 2 hours, THF was removed under vacuo and 1N HCl was added. The mixture was extracted with ethyl acetate, dried with anhydrous $Na_2SO_4$, filtered, concentrated under vacuo to provide the title compound. MS (ESI(+)) m/e 258 $(M+H)^+$, 375 $(M+NH_4)^+$, 380 $(M+Na)^+$; $^1$H NMR (500 MHz, DMSO-$d_6$) δ 10.14 (s, 1H), 8.20 (s, 1H), 7.70 (d, 1H, J=8.1 Hz), 7.60 (d, 1H, J=8.1 Hz), 7.47 (t, 1H, J=8.0 Hz), 7.20 (s, 1H), 4.40 (br d, 1H, J=12.8 Hz), 3.88 (br d, 1H, J=13.4 Hz), 3.08 (br t, 1H, J=12.9 Hz), 2.60 (m, 2H), 2.01 (s, 3H), 1.84 (m, 2H), 1.60 (m, 1H, 1.44 (m, 1H).

Example 5

5-(3-((2-(3-hydroxy-2-((methylamino)carbonyl)phenoxy)ethyl)amino)phenyl)isoxazole-3-carboxylic acid

Example 5A

2,6-dihydroxybenzamide

The mixture of 2,6-dihydroxybenzoate (168 mg, 1.0 mmol) and 2M methylamine in THF (3 mL, 6.0 mmol) in a sealed tube was heated at 100° C. overnight. The reaction mixture was then concentrated under reduced pressure and purified by flash chromatography on silica gel with hexane/ethyl acetate (1:1) to provide the titled compound (67 mg) as white solid. MS (ESI(+)) m/e 168 $(M+H)^+$; $^1$H NMR (300 MHz, DMSO-$d_6$) δ 12.57(bs, 2H), 8.82 (bs, 1H), 7.14 (t, J=8.1 Hz 1H), 6.35 (d, J=8.5 Hz, 2H), 2.85(d, J=4.7 Hz, 3H).

Example 5B

2-hydroxy-6-{2-((3-iodophenyl)amino)ethoxy}-N-methylbenzamide

The titled compound was prepared according to the procedure described in Example 1D, substituting 2-((3-iodophenyl)amino)ethanol for ethyl 5-(3-((1E)-3-hydroxyprop-1-enyl)phenyl)isoxazole-3-carboxylate, and dihydroxybenzamide for 2,6-dihydroxybenzoate.

Example 5C ethyl 5-{3-((2-{3-hydroxy-2-((methylamino)carbonyl)phenoxy}ethyl)amino)phenyl}isoxazole-3-carboxylate The titled compound was prepared according to the procedure described in Example 1E, substituting 2-hydroxy-6-{2-((3-iodophenyl)amino)ethoxy}-N-methylbenzamide for Example 1B.

Example 5D

5-{3-((2-{3-hydroxy-2-((methylamino)carbonyl)phenoxy}ethyl)amino)phenyl}isoxazole-3-carboxylic acid The titled compound was prepared according to the procedure described in Example 1F, substituting ethyl 5-{3-((2-{3-hydroxy-2-((methylamino)carbonyl)phenoxy}ethyl)amino)phenyl}isoxazole-3-carboxylate for ethyl 5-(3-((1E)-3-(3-hydroxy-2-(methoxycarbonyl)phenoxy)prop-1-enyl)phenyl)isoxazole-3-carboxylate. MS (ESI(+)) m/e 398 $(M+H)^+$; $^1$H NMR (300 MHz, DMSO-$d_6$) δ 13.69 (s, 1H), 7.30 (t, J=7.8 Hz, 1H), 7.23 (t, J=7.8 Hz, 1H), 7.10 (s, 1H), 7.05 (d, J=8.4 Hz, 1H), 6.83 (brs, 1H), 6.77 (dd, J=8.7, 2.4 Hz, 1H), 6.63 (dd, J=8.7, 1.2 Hz, 1H), 6.50 (dd, J=8.7, 1.2 Hz, 1H), 6.20 (t, J=5.4 Hz, 1H), 4.32 (t, J=5.1 Hz, 2H), 3.58 (q, J=5.1 Hz, 2H), 2.72 (d, J=4.5 Hz, 3H).

Example 6

5-(3-((1E)-3-(3-hydroxy-2-((methylamino)carbonyl)phenoxy)prop-1-enyl)phenyl)isoxazole-3-carboxylic acid The titled compound was prepared according to the procedure described in Example 1E–F, substituting the dihydroxybenzamide from Example 5A for 2,6-dihydroxybenzoate. MS (ESI(+)) m/e 395 $(M+H)^+$; $^1$H NMR (500 MHz, DMSO-$d_6$) δ 13.54 (s, 1H), 8.63–8.59 (m, 1H), 8.08(s, 1H), 7.84(d, J=7.8 Hz, 1H), 7.64(d, J=7.8 Hz, 1H), 7.54(t, J=7.8 Hz, 1H), 7.48(s, 1H), 7.29(t, J=8.4 Hz, 1H), 6.83 (d, J=16.2 Hz, 1H), 6.75 (dt, $J_1$=16.2 Hz, $J_2$=5.3 Hz, 1H), 6.64(d, J=8.4 Hz, 1H), 6.50(d, J=8.4 Hz, 1H), 4.96(d, J=5.0 Hz, 2H), 2.87(d, J=4.7 Hz, 1H).

Example 7

5-(3-(3-(3-hydroxy-2-(methoxycarbonyl)phenoxy)propyl)phenyl)isoxazole-3-carboxylic acid

Example 7A

3-(3-iodophenyl)propionic acid

To a stirred solution of (3-aminophenyl)propionic acid (4.91 g, 29.7 mmol) in water (50 mL) and concentrated $H_2SO_4$ (4 mL) at −7° C. (ice-salt bath) was added a solution of $NaNO_2$ (2.4 g, 34.7 mmol) in a minimum amount of water, expelling the nitrite solution below the surface of the solution and keeping the temperature below 0° C. After 10 minutes, the mixture was checked for the presence of excess $NO_2^-$ with starch-KI indicator paper to assure that diazotization was complete. Diethyl ether (50 mL) was added followed by a solution of KI (15 g, 90 mmol) in a minimum amount of water was added slowly to control the vigorous evolution of $N_2$. After addition was complete, the reaction was stirred and allowed to warm to ambient temperature over 3 hours. The layers were separated, the aqueous layer was extracted with additional diethyl ether (2×50 mL). The combined ether layers were back extracted with 5% (w/v) $NaHSO_{3(aq)}$, brine (1×25 mL), dried over $MgSO_4$, filtered, and concentrated to provide the titled compound (8.0 g). $^1$H NMR (300 MHz, $d_6$-DMSO) δ 12.13 (bs, 1H), 7.62 (d, 1H, J=1.7 Hz), 7.55 (dd, 1H, J=1.4, 6.4 Hz), 7.26 (d, 1H, J=7.4 Hz), 7.09 (t, 1H, J=7.6 Hz), 2.78 (t, 3H, J=7.6 Hz), 2.53 (t, 3H, J=7.5 Hz); MS (ESI) m/z 275 (M−H).

Example 7B 3-(3-iodophenyl)-1-propanol

To an ice cooled solution of 3-(3-iodophenyl)propionic acid (8.0 g, 29.7 mmol) in THF (30 mL) was added 1.0 M BH$_3$ in THF (40 mL, 40 mmol). The mixture was stirred at 0° C. for 1 hour, then quenched by careful addition of 1:1 THF:H$_2$O (10 mL). The mixture was concentrated in vacuo, the residue taken up in diethyl ether (100 mL), washed with water (1×100 mL, 1×50 mL), and brine (1×25 mL), dried over MgSO$_4$, filtered, and concentrated to an oil. The oil was purified via silica gel chromatography, eluting with 40% ethyl acetate in hexanes to provide the titled compound (6.3 g, 81%). $^1$H NMR (300 MHz, d$_6$-DMSO) δ 7.58 (d, 1H, J=1.4 Hz), 7.53 (ddd, 1H J=1.0, 1.7, 6.1 Hz), 7.22 (dd, 1H, J=1.7, 6.4 Hz), 7.08 (t, 1H, J=7.6 Hz), 4.47 (t, 1H, J=5.1 Hz), 3.38 (dt, 2H, J=5.1, 6.3 Hz), 2.57 (t, 2H, J=7.8 Hz), 1.68 (m, 2H); MS (ESI) m/z 279 (M+NH$_4$).

Example 7C 5-(3-(3-Hydroxy-propyl)-phenyl)-isoxazole-3-carboxylic acid ethyl ester To 3-(3-iodophenyl)-1-propanol (1.55 g, 5.60 mmol), tri-2-furylphosphine (130 mg, 0.56 mmol), tris(dibenzylideneacetone)dipalladium (256 mg, 0.23 mmol), and CuI (107 mg, 0.56 mmol) was added DMF (10 mL). To this mixture was added a solution of 5-tributylstannanyl-isoxazole-3-carboxylic acid ethyl ester (2.41 g, 5.60 mmol) as a solution in DMF (10 mL). The reaction was stirred under N$_2$ at ambient temperature for 1 hour, then 5% (w/v) KF$_{(aq)}$ (100 mL) and diethyl ether (50 mL) were added. The biphasic mixture was stirred vigorously for 10 minutes, then filtered through diatomaceous earth to remove the solid precipitates. The precipitate was washed with diethyl ether to recover any organic material from the filter pad, then the combined filtrate and washings were separated. The aqueous layer was extracted with additional ether (2×25 ML), the combined ether layers were washed with water (1×25 mL), and brine (1×25 mL), dried over MgSO$_4$, filtered, and concentrated to an oil. The product was purified via silica gel chromatography, eluting with 40% ethyl acetate/hexanes to provide the titled compound (950 mg, 2%). $^1$H NMR (500 MHz, d$_6$-DMSO) δ 7.81 (s, 1H), 7.77 (d, 1H, J=7.5 Hz), 7.47 (t, 1H, J=7.6 Hz), 7.47 (s, 1H), 7.39 (d, 1H, J=7.4 Hz), 4.49 (t, 1H, J=5.2 Hz), 4.41 (q, 2H, J=7.2 Hz), 3.44 (q, 2H, J=5.9 Hz), 2.71 (t, 2H, J=7.8 Hz), 1.78 (m, 2H), 1.36 (t, 3H, J=7.2 Hz); MS (ESI) m/z 276 (M+H)$^+$, 293 (M+NH$_4$)$^+$, 298 (M+Na)$^+$.

Example 7D

5-{3-(3-(3-Hydroxy-2-methoxycarbonyl-phenoxy)-propyl)-phenyl}-isoxazole-3-carboxylic acid To 5-(3-(3-hydroxy-propyl)-phenyl)-isoxazole-3-carboxylic acid ethyl ester (31 mg, 0.1 mmol) was added triphenylphosphine (29 mg, 0.11 mmol), methyl (2,6-dihydroxy)benzoate (20 mg, 0.12 mmol), then THF (1 mL). After the solids had dissolved, diethylazodicarboxylate (20 μL, 0.13 mmol) was added, and the reaction was stirred at ambient temperature for 1 hour. The reaction was concentrated in vacuo, and the residue was taken up in aqueous 2M NaOH (1 mL), along with enough methanol to make the solution homogeneous. After stirring for 10 minutes, the solvents were removed in vacuo, glacial acetic acid (4 drops) was added, and the product was purified by reverse phase HPLC, eluting with a acetonitrile/0.1% aq. trifluoroacetic acid gradient to provide the title compound (2.7 mg, 7%). $^1$H NMR (500 MHz, d$_6$-DMSO) δ 9.94 (s, 1H), 7.79 (s, 1H), 7.76 (d, 1H, J=7.8 Hz), 7.46 (t, 1H, J=7.6 Hz), 7.37 (d, 1H, J=7.5 Hz), 7.34 (s, 1H), 7.15 (t, 1H, J=8.3 Hz), 6.49 (dd, 2H, J=2.8, 8.4 Hz), 3.95 (t, 2H, J=6.2 Hz), 3.79 (s, 3H), 2.78 (t, 2H, J=7.5 Hz), 2.01 (m, 2H); MS (ESI) m/z 398 (M+H), 415 (M+NH$_4$).

Example 8

5-(2-fluoro-5-((1E)-3-(3-hydroxy-2-(methoxycarbonyl)phenoxy)prop-1-enyl)phenyl)isoxazole-3-carboxylic acid

Example 8A 4-fluoro-3-iodobenzaldehyde

A mixture of 4-fluoro-3-iodotoluene (5.0 g, 21.2 mmol) and NBS (4.2 g, 23.3 mmol) in 50 mL of CCl$_4$ was refluxed under N$_2$ with benzoyl peroxide (250 mg, 1.03 mmol) was heated for 3 hours. The reaction mixture was cooled to room temperature and filtered through celite, washed with benzene. The filtrate was evaporated and pumped to give the benzylbromide as a crude light brown oil.

A mixture of benzylbromide in 50 mL of DMSO was heated with NaHCO$_3$ solid (3.55 g, 42.2 mmol) at 120° C. for 90 min. The reaction mixture was then cooled to room temperature, quenched with water, extracted with Et$_2$O, and washed with water, brine. The organic layer was dried with Na$_2$SO$_4$, concentrated in vacuuo. MPLC purification provided the titled compound as a colorless oil which solidified over time (2.2 g, 41.5% over two steps).

Example 8B 5-(2-fluoro-5-((1E)-3-(3-hydroxy-2-(methoxycarbonyl)phenoxy)prop-1-enyl)phenyl)isoxazole-3-carboxylic acid The titled compound was prepared according to the procedure described in Example 1A–F, substituting the 3-iodobenzaldehyde for 3-iodo-4-fluorobenzaldehyde from Example 8A. MS (ESI(+)) m/e 414 (M+H)$^+$; $^1$H NMR (300 MHz, DMSO-d$_6$) δ 9.98 (s, 1H), 8.05 (dd, J=6.9 Hz, 1H), 7.78–7.69 (m, 1H), 7.45 (dd, J=8.7, 11.4 Hz, 1H), 7.22 (d, J=2.7 Hz, 1H), 7.18 (d, J=8.7 Hz, 1H), 6.79 (d, J=15.9 Hz, 1H), 6.60 (d, J=8.7 Hz, 1H), 6.52 (d, J=8.7 Hz, 1H), 4.74 (d, J=5.1 Hz, 2H), 3.79 (s, 3H).

Example 9

5-(3-((1E)-3-(3-hydroxy-2-nitrophenoxy)prop-1-enyl)phenyl)isoxazole-3-carboxylic acid The titled compound was prepared according to the procedure described in Example 1F, substituting 2-nitroresorcinol for 2,6-dihydroxybenzoate. MS (ESI(+)) m/e 400 (M+18)$^+$; $^1$H NMR (500 MHz, DMSO-d$_6$) δ 10.92 (s, 1H), 8.07(s, 1H), 7.84(d, J=7.8 Hz, 1H), 7.62(d, J=7.8 Hz, 1H), 7.54(t, J=7.8 Hz, 1H), 7.49(s, 1H), 7.30(t, J=8.4 Hz, 1H), 6.83–6.75(m, 2H), 6.68–6.62(m, 2H), 4.86(d, J=5.0 Hz, 2H).

Example 10

5-(3'-(3-(carboxy)isoxazol-5-yl)-1,1'-biphenyl-3-yl)isoxazole-3-carboxylic acid

Example 10A methyl 5-(3-iodophenyl)isoxazole-3-carboxylate

The titled compound was prepared according to the procedure described in Example 2A–B, substituting the 3'-bromoacetophenone with 3'-iodoacetophenone.

Example 10B 2,2-dimethyl-4-vinyl-1,3-dioxolane

3-Butene-1,2-diol (5.00 g, 56.7 mmol), acetone (9.88 g, 170 mmol), 2,2-dimethoxy propane (17.7 g, 170 mmol), and p-toluene sulfonic acid (1.62 g, 8.5 mmol) were added to benzene (100 mL). After 16 hours of reflux, starting material was observed by TLC. 2,2-Dimethoxy propane (9.99 g, 95.1 mmol) and acetone (1.58 g, 27.3 mmol) were then added, followed by an additional 3 hour reflux. The mixture was washed with saturated aqueous $NaHCO_3$ and extracted with EtOAc (3×40 mL). The organic extracts were dried over $MgSO_4$, filtered, concentrated and purified by column chromatography (5% ethyl acetate in hexanes) to provide the titled compound (4.12 g, 57%) as a light yellow oil.

Example 10C

Methyl 5-(3'-(3-(methoxycarbonyl)isoxazol-5-yl)-1,1'-biphenyl-3-yl)isoxazole-3-carboxylate The iodide from Example 16A (1.04 g, 3.16 mmol) and the acetonide from Example 16B (0.613 g, 4.79 mmol), P(o-tolyl)$_3$ (97 mg, 0.64 mmol, 20 mol %), and Et$_3$N (0.322 g, 3.2 mmol) were added to DMF(3 mL). The mixture was flushed with N$_2$ for 30 min., Pd(OAc)$_2$ (72 mg, 0.32 mmol, 10 mol %) was added, and the reaction was heated to 100° C. in a sealed culture tube for 3 hours. After work up, the mixture was purified by column chromatography (10% ethyl acetate in hexanes) to provide the titled compound (150 mg, 12%).

Example 10D 5-(3'-(3-(carboxy)isoxazol-5-yl)-1,1'-biphenyl-3-yl)isoxazole-3-carboxylic acid The ester from Example 10C (65 mg, 0.16 mmol) was dissolved in 4M NaOH (5 mL) in MeOH/H$_2$O (5:3). After 2 hours no starting material was visible by TLC. When the reaction mixture was acidified to pH 1, the product precipitated out. The titled compound (22 mg, 36%) was obtained after reverse phase HPLC (0–70% acetonitrile in 0.1% aqueous TFA) as a white solid. MS (DEI) positive ion; m/z 376 (M)$^+$: negative ion; m/z 751.1 (2M–H)$^-$, 375.1 (M–H)$^-$. $^1$H NMR (300 MHz, DMSO-d$_6$) δ 7.6 (s, 2H), 7.7 (t, J=7.8 Hz, 2H), 8.0 (dd, J=8.1, 1.5 Hz, 4H), 8.3 (s, 2H), 14.0 (br s, 2H).

Example 11

5-(3-((1S,2S)-2-((3-hydroxy-2-(methoxycarbonyl)phenoxy)methyl)cyclopropyl)phenyl)isoxazole-3-carboxylic acid

Example 11A ethyl (1R,2R)-2-(3-iodophenyl)cyclopropanecarboxylate

Me$_3$SOI (379 mg, 1.72 mmol) was suspended in 3 mL of DMSO. NaH (60% suspension in mineral oil, 70 mg, 1.72 mmol) was added. Stirred at room temperature before the 3-iodoethyl cinnamate (400 mg, 1.32 mmol) from Example 1A was added. The resulting mixture was heated at 65° C. for 20 minutes before it was stirred at room temperature for 2 hours. The resulting mixture was then worked up by partitioning between diethyl ether and water. The organic layer was washed with water and brine, dried over MgSO$_4$, filtered, evaporated to provide the titled compound (127 mg, 31.8 mmol) as a light brown oil.

Example 11B 5-(3-((1S,2S)-2-((3-hydroxy-2-(methoxycarbonyl)phenoxy)methyl)cyclopropyl)phenyl)isoxazole-3-carboxylic acid The titled compound was prepared according to the procedure described in Example 1B–F, substituting iodocinnamate from Example 1A for the iodide from Example 11A. MS (ESI(+)) m/e 410 (M+H)$^+$; $^1$H NMR (300 MHz, DMSO-d$_6$) δ 9.93 (s, 1H), 7.72 (d, J=7.6 Hz, 1H), 7.66 (s, 1H), 7.45 (s, 1H), 7.44 (t, J=7.6 Hz, 1H), 7.29 (d, J=8.4 Hz, 1H), 7.17 (t, J=8.4 Hz, 1H), 6.53 (d, J=8.4 Hz, 1H), 6.49 (d, J=8.4 Hz, 1H), 4.09 (dd, J=11.1, 6.9 Hz, 1H), 3.96 (dd, J=11.1, 6.9 Hz, 1H), 3.70 (s, 3H), 2.05 (dt, J=8.4, 4.2 Hz, 2H), 1.66–1.51 (m, 2H), 1.15 (dt, J=9.3, 7.2 Hz, 1H), 1.07 (dt, J=9.3, 7.2 Hz, 1H).

Example 12

5-(3-(3-(3-hydroxy-2-(methoxycarbonyl)phenoxy)butyl)-4-methoxyphenyl)isoxazole-3-carboxylic acid

Example 12A methyl 5-(3-bromo-4-methoxyphenyl)isoxazole-3-carboxylate

The titled compound was prepared according to the procedure described in Example 2A–B, substituting 3'-bromoacetophenone with 3'-bromo-4'-fluoroacetophone. A mixture of two products was separated by MPLC to give the titled compound.

Example 12B 5-(3-(3-(3-hydroxy-2-(methoxycarbonyl)phenoxy)butyl)-4-methoxyphenyl)isoxazole-3-carboxylic acid The titled compound was prepared according to the procedure described in Example 2C–F, substituting the bromide from Example 2B with the bromide from Example 12A. MS (ESI(+)) m/e 442 (M+H)$^+$; $^1$H NMR (300 MHz, DMSO-d$_6$) δ 9.89 (s, 1H), 7.78 (dd, J=7.5, 2.4 Hz, 1H), 7.67

(d, J=2.4 Hz, 1H), 7.16 (s, 1H), 7.12 (t, J=7.5 Hz, 1H), 7.10 (d, J=9.0 Hz, 1H), 6.47 (d, J=3.6 Hz, 1H), 6.44 (d, J=3.6 Hz, 1H), 4.37 (sextet, J=6.0 Hz, 1H), 3.83 (s, 3H), 3.76 (s, 3H), 2.58–2.82 (m, 2H), 1.97–1.73 (m, 2H), 1.25 (d, J=6.0 Hz, 3H).

Example 13

5-(4-fluoro-3-(3-(3-hydroxy-2-(methoxycarbonyl) phenoxy)butyl)phenyl)isoxazole-3-carboxylic acid Example 13A methyl 5-(3-bromo-4-fluorophenyl)isoxazole-3-carboxylate The titled compound was prepared according to the procedure described in Example 2A–B, substituting 3'-bromoacetophenone with 3'-bromo-4'-fluoroacetophone. A mixture of two products was separated by MPLC to give the titled compound.

Example 13B 5-(4-fluoro-3-(3-(3-hydroxy-2-(methoxycarbonyl) phenoxy)butyl)phenyl)isoxazole-3-carboxylic acid The titled compound was prepared according to the procedure described in Example 2C–F, substituting the bromide from Example 2B with the bromide from Example 13A. MS (ESI(+)) m/e 430 (M+H)$^+$; $^1$H NMR (300 MHz, DMSO-d$_6$) δ 9.91 (s, 1H), 7.89-7.79 (m, 2H), 7.35 (dd, J=9.0, 8.7 Hz, 1H), 7.12 (t, J=8.3 Hz, 1H), 6.49 (d, J=4.0 Hz, 1H), 6.45 (d, J=4.0 Hz, 1H), 4.42 (sextet, J=6.0 Hz, 1H), 3.75 (s, 3H), 2.65–2.90 (m, 2H), 1.81–1.95 (m, 2H), 1.25 (d, J=6.0 Hz, 1H).

Example 14

5-(3-(3-(3-hydroxy-2-(methoxycarbonyl)phenoxy) pentyl)phenyl)isoxazole-3-carboxylic acid The titled compound was prepared according to the procedure described in Example 3C–F, substituting 3-buten-2-ol used in Example 33C with 1-penten-3-ol. MS (ESI(+)) m/e 426 (M+H)$^+$; $^1$H NMR (300 MHz, DMSO-d$_6$) δ 9.89 (s, 1H), 7.73–7.89 (m, 2H), 7.45 (t, J=7.8 Hz, 1H), 7.36 (s, 1H), 7.33 (d, J=8.25 Hz, 1H), 7.10 (t, J=8.25 Hz, 1H), 6.46 (d, J=6.6 Hz, 1H), 6.43 (d, J=6.6 Hz, 1H), 4.26 (quintet, J=5.8 Hz, 1H), 3.76 (s, 3H), 2.61–2.83 (m, 2H), 1.82–1.97 (m, 2H), 1.58–1.70 (m, 2H), 0.89 (t, J=7.65 Hz, 3H).

Example 15

5-(3-((1E)-3-(3-hydroxy-2-propionylphenoxy)prop-1-enyl)phenyl)isoxazole-3-carboxylic acid The titled compound was prepared according to the procedure described in Example 1F, substituting 1-(2,6-dihydroxy-phenyl)-propan1-one for 2,6-dihydroxybenzoate. MS (ESI(+)) m/e 411 (M+18)$^+$; $^1$H NMR (500 MHz, DMSO-d$_6$) δ 14.05 (bs, 1H), 8.07 (s, 1H), 10.94 (s, 1H), 7.84 (d, J=7.8 Hz, 1H), 7.62(d, J=7.8 Hz, 1H), 7.54(t, J=7.8 Hz, 1H), 7.47(s, 1H), 7.24(t, J=8.4 Hz, 1H), 6.82 (d, J=16.0 Hz, 1H), 6.70 (dt, J$_1$=16.0 Hz, J$_2$=5.5 Hz, 1H), 6.63(d, J=8.0 Hz, 1H), 6.51(d, J=8.0 Hz, 1H), 4.80 (d, J=4.6 Hz, 2H), 2.88 (q, J=7.4 Hz, 2H), 1.06(t, J=7.4 Hz, 3H).

Example 16

5-(3-((1E)-4-hydroxy-3-(3-hydroxy-2-(methoxycarbonyl)phenoxy)but-1-enyl)phenyl)isoxazole-3-carboxylic acid Example 16A 1-((tert-butyl(dimethyl)silyl)oxy)but-3-en-2-ol t-Butyl dimethylsilylchloride (4.28 g, 28.4 mmol) and imidazole (4.83 g, 70.9 mmol) were added to a flask purged with N$_2$ and dichloromethane (50 mL) was added. 3-Butene-1,2-diol (2.50 g, 28.4 mmol) was then added to the flask and the mixture was stirred for 2 hours. The solvent was removed and the titled product (2.71 g, 47.9%) was purified by column chromatography (5% ethyl acetate in hexanes).

Example 16B methyl 2-((1-(((tert-butyl(dimethyl)silyl)oxy)methyl)prop-2-enyl)oxy)-6-hydroxybenzoate A solution of alcohol from Example 16A (2.65 g, 13.1 mmol), methyl-2,6-dihydroxybenzoate (3.51 g, 20.9 mmol), PPh$_3$ (3.34 g, 15.7 mmol), and TBF (20 mL) was cooled to 0° C. Diethylazodicarboxylate (2.51 g, 14.4 mmol) was added. The reaction was allowed to warm to room temperature and stir for 16 hours. The titled product (1.11 g, 24%) was obtained following silica gel column chromatography (10% ethyl acetate in hexanes).

Example 16C methyl 5-(3-((1E)-4-((tert-butyl(dimethyl)silyl)oxy)-3-(3-hydroxy-2-(methoxycarbonyl)phenoxy)but-1-enyl)phenyl)isoxazole-3-carboxylate The allyl ether from Example 16B (1.102 g, 3.13 mmol) and iodide from Example 10A (1.027 g, 3.12 mmol), P(o-tolyl)$_3$ (0.038 g, 4 mol %), Et$_3$N (0.322 g, 3.2 mmol), and DMF (3 mL) were added to a culture tube. Nitrogen was bubbled through the solution for 20 min, followed by the addition of Pd(OAc)$_2$ (0.014 g, 2 mol %). The tube was then capped and the mixture heated to 80° C. for 3 hours. The crude mixture was separated by column chromatography (10% ethyl acetate in hexanes) to provide the titled compound.(0.320 g, 19%).

Example 16D 5-(3-((1E)-4-hydroxy-3-(3-hydroxy-2-(methoxycarbonyl)phenoxy)but-1-enyl)phenyl)isoxazole-3-carboxylic acid To a 4M NaOH solution (3 mL) in MeOH/H$_2$O (5:3) solution was added the ester from Example 18C (50 mg, 0.090 mmol). The mixture was stirred for 2 hours. The reaction was then acidified to pH 3–4 and allowed to stir for 1 hour. Purification was performed by reverse phase HPLC (0–70% acetonitrile in 0.1% aqueous TFA) to yield the titled compound (0.005 g, 13%) as a white solid. MS (ESI) positive ion; m/z 448 (M+Na)$^+$, 443 (M+NH$_4$)$^+$, 426 (M+H)$^+$: negative ion; m/z 424 (M–H)$^-$, 380 (M–CO$_2$H)$^-$. $^1$H NMR (500 MHz, DMSO-d$_6$) δ 3.6 (dd 1H, J=5, 11 Hz, 1H), 3.6 (dd 1H, J=5, 11 Hz, 1H), 3.7 (s, 3H), 4.8 (ddd, J=5.5, 5.5, 6 Hz, 1 H), 6.4 (d, J=8.5 Hz, 1H), 6.4 (dd, 6.5, 16.5 Hz, 1H), 6.6 (d, J=8.5 Hz, 1 H), 6.7 (d, J=16.5 Hz, 1H), 7.1 (t, J=8.5, 1H), 7.4 (s, 1H), 7.5 (t, J=7.5 Hz, 1H), 7.5 (d, J=8 Hz, 1H), 7.8 (d, J=7.5, 1H), 8.0 (s, 1H), 9.9 (s, 1H), 14.0 (br s, 1H).

Example 17

5-(1-(2-(3-hydroxy-2-(methoxycarbonyl)phenoxy) ethyl)-1H-indol-6-yl)isoxazole-3-carboxylic acid

Example 17A 2-(6-bromo-1H-indol-1-yl)ethanol

KOH (571 mg, 10.2 mmol) was stirred in 5 mL of anhydrous DMSO at room temperature. 6-Bromoindole (500 mg, 2.55 mmol) was added as solid. After 30 min, 2-bromoethanol (181 µL, 2.55 mmol) was added to the green solution, which was then stirred at room temperature overnight. Water was then added and the reaction mixture was extracted with ethyl acetate (2×25 mL). The organic layer was then washed with water and brine, dried over $Na_2SO_4$, evaporated in vacuo. MPLC purification of the crude product provided the titled compound as a light brown oil (344 mg, 56% yield).

Example 17B ethyl 5-(1-(2-hydroxyethyl)-1H-indol-6-yl)isoxazole-3-carboxylate The titled compound was prepared according to the procedure described in Example 21D, substituting the bromide from Example 21C for the bromide from Example 17A, and the 3-tributylstannyl-1-propanol for Example 1C.

Example 17C 5-(1-(2-(3-hydroxy-2-(methoxycarbonyl)phenoxy) ethyl)-1H-indol-6-yl)isoxazole-3-carboxylic acid The titled compound was prepared according to the procedure described in Example 1E–F, substituting the allyl alcohol from Example 1D for the alcohol from Example 17B. MS (ESI(+)) m/e 423 (M+H)$^+$; $^1$H NMR (300 MHz, DMSO-d$_6$) δ 9.95 (s, 1H), 8.17 (s, 1H), 7.69 (d, J=8.4 Hz, 1H), 7.57 (dd, J=8.4, 1.5 Hz, 1H), 7.49 (d, J=3.1 Hz, 1H), 7.25 (s, 1H), 7.13 (t, J=8.6 Hz, 1H), 6.54 (d, J=3.1 Hz, 1H), 6.49 (s, 1H), 6.46 (s, 1H), 4.63 (t, J=5.1 Hz, 2H), 4.29 (t, J=5.1 Hz, 2H), 3.61 (s, 3H).

Example 18

5-(3-((1E)-3-(2-(acetylamino)-3-hydroxyphenoxy) prop-1-enyl)phenyl)isoxazole-3-carboxylic acid

Example 18A

N-(2,6-dihydroxyphenyl)acetamide

A mixture of 2-nitroresorcinol (1.0 g, 6.45 mmol) and 10% Pd—C (100 mg) in methanol (15 mL) was stirred under an atmosphere of hydrogen at ambient temperature for 4 hours. The reaction mixture was filtered and concentrated to get desired aniline. The aniline was then dissolved in dichloromethane (15 mL). Triethylamine (1.8 mL, 12.9 mmol) was added, followed by acetyl chloride (1.38 mL, 19.35 mmol). The reaction mixture was stirred at ambient temperature for 1 hour, and added 20 mL 1N NaOH and methanol (20 mL). After 10 minutes, the mixture was concentrated and taken in ethyl acetate and 1N HCl. The organic phase was washed with brine, dried (MgSO$_4$), filtered and concentrated to provide titled compound. MS (ESI (+)) m/e 168(M+H)$^+$; $^1$H NMR (300 MHz, DMSO-d$_6$) δ 9.31(s, 2H), 6.86 (t, J=8.1 Hz, 1H), 6.34 (d, J=8.1 Hz, 2H), 2.11(s, 3H).

Example 18B 5-(3-((1E)-3-(2-(acetylamino)-3-hydroxyphenoxy) prop-1-enyl)phenyl)isoxazole-3-carboxylic acid The titled compound was prepared according to the procedure described in Example 1F, substituting Example 18A for 2,6-dihydroxybenzoate. MS (ESI(+)) m/e 412 (M+18)$^+$; $^1$H NMR (500 MHz, DMSO-d$_6$) δ 9.14 (s, 1H), 8.05(s, 1H), 7.83(d, J=7.8 Hz, 1H), 7.61(d, J=7.8 Hz, 1H), 7.54(t, J=7.8 Hz, 1H), 7.47(s, 1H), 7.03(t, J=8.1 Hz, 1H), 6.85 (d, J=16.2 Hz, 1H), 6.68(dt, J$_1$=16.2 Hz, J$_2$=5.3 Hz, 1H), 6.60(d, J=8.1 Hz, 1H), 6.50(d, J=8.1 Hz, 1H), 4.75(d, J=4.4 Hz, 2H), 2.09(s, 3H).

Example 19

5-(3-((1E)-3-(2-((benzylamino)carbonyl)-3-hydroxyphenoxy)prop-1-enyl)phenyl)isoxazole-3-carboxylic acid

Example 19A

N-benzyl-2,6-dihydroxybenzamide

The titled compound was prepared according to the procedure described in Example 6A, substituting benzyl amine for methylamine. MS (ESI(+)) m/e 244 (M+H)$^+$.

Example 19B 5-(3-((1E)-3-(2-((benzylamino)carbonyl)-3-hydroxyphenoxy)prop-1-enyl)phenyl)isoxazole-3-carboxylic acid The titled compound was prepared according to the procedure described in Example 1F, substituting Example 19A for 2,6-dihydroxybenzoate. MS (ESI(+)) m/e 471 (M+H)$^+$; $^1$H NMR (500 MHz, DMSO-d$_6$) δ 13.03 (s, 1H), 9.05–8.97 (m, 1H), 8.01(s, 1H), 7.88–7.83 (m, 1H), 7.54(d, J=5.2 Hz, 2H), 7.44(s, 1H), 7.36–7.28(m, 3H), 7.22–7.10(m, 3H), 6.86–6.52(m, 4H), 4.91(d, J=5.8 Hz, 2H), 4.91(d, J=5.8 Hz, 2H), 4.55(d, J=5.8 Hz, 2H).

Example 20

5-(3-((1E)-3-(3-hydroxy-2-(methoxycarbonyl)-4-nitrophenoxy)prop-1-enyl)phenyl)isoxazole-3-carboxylic acid

Example 20A methyl 2,6-dihydroxy-3-nitrobenzoate

1M HNO$_3$ in acetic acid (10 mL, 10.0 mmol) was added dropwise to a solution of 2,6-dihydroxybenzoate (1.68 g, 10.0 mmol) in acetic acid (10 mL) at ambient temperature. The reaction mixture was stirred for 2 hours. The precipitant was filtered and washed with water and acetone, dried to provide the titled compound (1.08 g). MS (ESI(−)) m/e 212 (M−H)$^+$; $^1$H NMR (300 MHz, DMSO-d$_6$) δ 11.71(bs, 1H), 10.93 (bs, 1H), 8.04 (d, J=9.5 Hz, 1H), 6.60(d, J=9.5 Hz, 1H).

Example 20B 5-(3-((1E)-3-(3-hydroxy-2-(methoxycarbonyl)-4-nitrophenoxy)prop-1-enyl)phenyl)isoxazole-3-carboxylic acid The titled compound was prepared according to the procedure described in Example 1F, substituting Example 20A for 2,6-dihydroxybenzoate. MS (ESI(+)) m/e 458 (M+18)$^+$; $^1$H NMR (500 MHz, DMSO-d$_6$) δ 14.03 (bs, 1H), 10.84 (bs, 1H), 8.18(d, J=9.7 Hz, 1H), 8.08(s, 1H), 7.85(d, J=7.8 Hz, 1H), 7.63(d, J=7.8 Hz, 1H), 7.54(t, J=7.8 Hz, 1H), 7.50(s, 1H), 6.96(d, J=9.7 Hz, 1H), 6.82(d, J=15.9 Hz, 1H), 6.67(dt, J$_1$=15.9 Hz, J$_2$=5.6 Hz, 1H), 4.97(d, J=5.0 Hz, 2H), 3.86(s, 3H).

Example 21

4-amino-5-(3-((1E)-3-(3-hydroxy-2-(methoxycarbonyl)phenoxy)prop-1-enyl)phenyl)isoxazole-3-carboxylic acid

Example 21A 1-(3-bromophenyl)-2-nitroethanone

To a solution of 3-bromobenzaldehyde (18.5 g, 100 mmol) in MeOH (100 mL) was added MeNO$_2$ (12.2 g, 200 mmol) at 0° C. followed by addition of KOH (11.2 g, 200 mmol). After 2 hours, MeOH was removed in vacuo and the resulting mixture was partitioned between ethyl acetate and water. Ethyl acetate extracts were dried over MgSO$_4$ and concentrated to give 20 g crude mixture. This crude mixture was dissolved in AcOH (200 mL), to which CrO$_3$ (12.0 g, 120 mmol) was added. Acetic acid was removed under vacuo after 2 hours and water (200 mL) was added and extracted with ethyl acetate (3×100 mL). The combined organic extracts were dried over MgSO$_4$, filtered and then concentrated under vacuo. dichloromethane (20 mL) was added and the titled compound (8.5 g, 35% for 2 steps) was precipitated out and collected by filtration.

Example 21B ethyl 5-(3-bromophenyl)-4-nitroisoxazole-3-carboxylate

To a suspension of compound from Example 21A (1.8 g, 7.3 mmol) in ethyl alcohol (15 mL) was added Et$_3$N (730 mg, 7.3 mmol) at 0° C. The mixture turned into a yellow, homogeneous solution, to which was added ethyl chlorooxamate (1.1 g, 7.3 mmol) in EtOH (5 mL) over 20 min between −15° C. and −10° C. The reaction mixture was concentrated after overnight stirring and purified by flash column chromatography (12% ethyl acetate in hexanes) to provide the titled compound (800 mg, 32%).

Example 21C ethyl 4-amino-5-(3-bromophenyl)isoxazole-3-carboxylate

This material from Example 21B was dissolved in a mixture of EtOH (6 mL) and water (2 mL). Ammonium chloride (160 mg, 3 mmol) and iron powder (1.6 g, 28 mmol) were added at r.t. The reaction mixture was filtered after 1 h. The filtrate was extracted with ethyl acetate (3×30 mL). The combined organic extracts were dried over MgSO$_4$, concentrated, and purified by flash column chromatography (20% ethyl acetate in hexanes) to provide the titled compound (390 mg, 17% for two steps).

Example 21D ethyl 4-amino-5-(3-((1E)-3-hydroxyprop-1-enyl)phenyl)isoxazole-3-carboxylate To a dioxane (4 mL) solution of compound from Example 21C (710 mg, 2.3 mmol) was added Pd$_3$(dba)$_2$-CHCl$_3$ (71 mg, 0.07 mmol, 3% equiv.) and CsF (760 mg, 5.1 mmol, 2.2 equiv.) under N$_2$. P($^t$Bu)$_3$ (10% in hexanes, 0.42 mL, 0.14 mmol, 12% equiv) and 3-tributylstannyl-1-propanol (1.1 g, 3.2 mmol, 1.1 equiv.) were added sequentially. The mixture was flushed with N$_2$ for 2 min and then heated to 100° C. in a sealed culture tube. The mixture was purified by flash column chromatography (50% ethyl acetate in hexanes) to provide the titled compound (150 mg, 22%).

Example 21E ethyl 4-amino-5-(3-((1E)-3-(3-hydroxy-2-(methoxycarbonyl)phenoxy)prop-1-enyl)phenyl)isoxazole-3-carboxylate To a THF (1 mL) solution of compound from Example 21D (150 mg, 0.52 mmol), methyl 2,6-dihydroxybenzoate (336 mg, 2.0 mmol), and PPh$_3$ (210 mg, 0.8 mmol) was added DEAD (140 mg, 0.8 mmol) at 0° C. Insoluble salt (phenolate/PPh$_3$) formed quickly. The mixture was warmed to ambient temperature and dichloromethane (3 mL) was added, but the salt remained insoluble in this solvent system. A drop of water was added after 2 hours to decompose the salt, upon which the slurry turned into a homogeneous solution. The mixture was purified by flash column chromatography (30% ethyl acetate in hexanes) to provide the titled compound (130 mg, 40%).

Example 21F 4-amino-5-(3-((1E)-3-(3-hydroxy-2-(methoxycarbonyl)phenoxy)prop-1-enyl)phenyl)isoxazole-3-carboxylic acid Compound from Example 21F was dissolved in a mixture of EtOH (1 mL) and water (0.6 mL) and aqueous NaOH (50%, 0.3 mL) was added at r.t. Aqueous HCl (10%) was added to the reaction mixture after 30 min. Yellow precipitates formed when pH1 was reached. The precipitates were collected and purified by reverse phase HPLC (0–70% acetonitrile in 0.1% aqueous TFA) to give the titled compound (14 mg, 16% for two steps). $^1$H NMR (500 MHz, CDCl$_3$) δ 9.97 (s, 1H), 7.79 (broad, s, 1H), 7.66 (ddd, J=2.5, 2.5, 7.0 Hz, 1H), 7.51 (m, 2H), 7.19 (t, J=8.5 Hz, 1H), 6.80 (d, J=16.0 Hz, 1H), 6.60 (d, J=8.0 Hz, 1H), 6.58 (td, J=5.5, 16.0 Hz, 1H), 6.51 (d, J=8.0 Hz, 1H), 4.51 (dm, J=5.5 Hz, 2H), and 3.78 (s, 3H). MS (ESI) positive ion 411 (M+H)$^+$, 433 (M+Na)$^+$: negative ion 409 (M−H)$^−$, 365 (M−CH$_3$)$^−$.

Example 22

5-(3-((1E)-3-((3',5-dihydroxy-4-(methoxycarbonyl)-1,1'-biphenyl-3-yl)oxy)prop-1-enyl)phenyl)isoxazole-3-carboxylic acid Example 22A 3,5-dimethoxyiodobenzene To an ice-salt cooled solution of 4.55 g (29.7 mmol) of 3,5-dimethoxyaniline in 50 mL of water was added 4 mL of 98% H$_2$SO$_4$. After the solution had cooled to −5° C., a solution of 2.4 g (34.8 mmol) of NaNO$_2$ in a minimum amount of water was added, keeping the temperature below 0° C. The reaction was stirred for 10 min, then 50 mL of diethyl ether was added. A solution of 15 g (90 mmol) of potassium iodide in a minimum amount of water was added slowly to control the evolution of N$_2$. After 3 h, the layers were separated, and the aqueous layer was extracted with additional ether (2×50 mL). The combined ether layers were back extracted with 5% (w/v) NaHSO$_3$(aq) (2×50 mL), 1 M HCl (1×50 mL), 2M NaOH (1×50 mL), then brine (1×25 mL), dried over MgSO$_4$, filtered, and concentrated to a dark oil. The product was purified by silica gel chromatography, eluting with 10% ethyl acetate:hexanes to provide the titled compound (4.80 g, 61%).

Example 22B 3,5,3'-Trimethoxybiphenyl

To a mixture of 600 mg (4.0 mmol) of 3-methoxyphenylboronic acid, 792 mg (3.0 mmol) of 3,5-dimethoxyiodobenzene, 34 mg (5 mol %) palladium(II)acetate, 182 mg (20 mol %) of tri-o-tolylphosphine, and 3.6 g (24 mmol) of cesium fluoride was added 10 mL of anhydrous dioxane. The reaction was stirred at reflux under N$_2$ for 50 min, then poured into 30 mL of water and extracted with diethyl ether (3×10 mL). The combined ether layers were back extracted with saturated aqueous NaHCO$_3$ solution (1×10 mL), then brine (1×10 mL), dried over MgSO$_4$, filtered, and concentrated to an oil. This was purified via silica gel chromatography, eluting with 10%, ethyl acetate:hexanes to provide the titled compound (650 mg, 89%).

Example 22C 3,5,3'-Trihydroxybiphenyl

To 395 mg (1.62 mmol) of 3,5,3'-trimethoxybiphenyl was added 9 mL of 1.0 M BBr$_3$ in CH$_2$Cl$_2$. The mixture was stirred at ambient temperature for 1.5 h, then poured over 60 mL of ice, and extracted with ethyl acetate (2×25 mL). The combined organic layers were back extracted with water (1×25 mL), then brine (1×25 mL), dried over MgSO$_4$, filtered, and concentrated to an oil. This was heated under vacuum at 110° C. to provide the titled compound (308 mg, 94%).

Example 22D 3,5,3'-trihydroxy-biphenyl-4-carboxylic acid methyl ester

To 308 mg (1.52 mmol) of 3,5,3'-trihydroxybiphenyl was added 400 mg (4.0 mmol) of KHCO$_3$, then 1 ml of glycerol. The reaction was stirred at 130° C. under 1 atm of CO$_2$ for 1 hour. Following this period of heating, the thick mixture was transferred to a sealed tube, the space above the mixture was purged with CO$_2$, then the reaction was heated at 120° C. for 15 hour, and at ambient temperature for 96 hours. The reaction was diluted with 10 mL of water, 5 mL of 1M HCl was added slowly, then the mixture was extracted with ethyl acetate (3×5 mL). The combined organic layers were back extracted with water (1×5 mL), and brine (1×5 mL), dried over MgSO$_4$, filtered, and concentrated to a dark residue. This was taken up in ethyl acetate and methanol, and treated with ethereal diazomethane until the acid was no longer visible by TLC and a new, higher R$_f$ spot appeared (40% ethyl acetate:hexanes). The product was purified by silica gel chromatography, eluting with 40% ethyl acetate:hexanes to give 100 mg (26%) of 3,5,3'-trihydroxy-biphenyl-4-carboxylic acid methyl ester as a white solid. $^1$H NMR (300 MHz, d$_6$-DMSO) δ 10.15 (bs, 2H), 9.56 (bs, 1H), 7.25 (t, 1H, J=7.8 Hz), 6.97 (dd, 1H, J=1.0, 9.2 Hz), 6.92 (t, 1H, J=2.0 Hz), 6.87 (dd, 1H, J=2.4, 8.0 Hz), 6.57 (s, 2H), 3.33 (s, 3H); MS (ESI) m/z=259 (M−H).

Example 22E

5-{3-(3-(5,3'-Dihydroxy-4-methoxycarbonyl-biphenyl-3-yloxy)-propenyl)-phenyl}-isoxazole-3-carboxylic acid The titled compound was prepared according to the procedure described in Example 1E-F, substituting the methyl 2,6-dihydroxybenzoate for the benzoate from Example 22D. $^1$H NMR (400 MHz, d$_6$-DMSO) δ 10.16 (s, 1H), 9.54 (s, 1H), 8.08 (s, 1H), 7.84 (d, 1H, J=7.7 Hz), 7.63 (d, 1H, J=8.0 Hz), 7.54 (t, 1H, J=7.8 Hz), 7.50 (s, 1H), 7.25 (t, 1H, J=7.8 Hz), 7.04 (dd, 1H, J=1.0, 7.7 Hz), 6.99 (t, 1H, J=2.0 Hz), 6.78–6.80 (m, 3H), 6.72 (d, 1H, J=1.2 Hz), 6.69 (dt, 1H, J=5.1, 16.0 Hz), 4.87 (d, 2H, J=4.9 Hz), 3.82 (s, 3H); MS (ESI) m/z=488 (M+H)$^+$, 505 (M+NH$_4$)$^+$.

Example 23

5-(3-{(1E)-3-(3-hydroxy-2-(methoxycarbonyl)phenoxy)prop-1-enyl}phenyl)-4-(hydroxymethyl)isoxazole-3-carboxylic acid Example 23A ethyl 3-(3-iodophenyl)-3-oxopropanoate Ethyl-3-iodobenzoate (25.4 g, 92.0 mmol) was dissolved in THF (60 mL) and cooled to 0° C. followed by the addition of KOt-Bu (20.6 g, 184 mmol). The mixture was stirred for 15 minutes followed by the addition of ethyl acetate (8.91 g, 101 mmol). The mixture was warmed to ambient temperature, stirred for 2 hours, diluted with aqueous HCl (10%, 200 mL) and extracted with ethyl acetate (2×150 mL). The combined organic layers were dried (Na$_2$SO$_4$), filtered and concentrated in vacuo to provide the titled compound (29.3 g, 100%).

Example 23B tert-butyl 3-(3-iodophenyl)-3-oxopropanoate

Ethyl 3-(3-iodophenyl)-3-oxopropanoate (29.3 g, 92.1 mmol) was heated to 120° C. in a sealed tube in t-butanol (80 mL) for 4 hours. The mixture was concentrated in vacuo and purified by column chromatography (0–3% ethyl acetate in hexanes) to provide the titled compound (12.1 g, 38%).

Example 23C

4-tert-butyl 3-ethyl 5-(3-iodophenyl)isoxazole-3,4-dicarboxylate tert-Butyl 3-(3-iodophenyl)-3-oxopropanoate (1.91 g, 5.52 mmol) was dissolved in ethanol (6 mL), cooled to 0° C., and $Et_3N$ (558 mg, 5.52 mmol) was added. After stirring 20 minutes, ethyl chlorooximidoacetate (836 mg, 5.52 mmol) in EtOH (3 mL) was added to the reaction mixture over 30 min. The reaction mixture was warmed to ambient temperature and stirred overnight. The mixture was concentrated in vacuo and purified by column chromatography (0–13% ethyl acetate in hexanes) to provide the titled compound (860 mg, 35%).

Example 23D ethyl 4-(hydroxymethyl)-5-(3-iodophenyl)isoxazole-3-carboxylate

To a solution of 4-tert-butyl 3-ethyl 5-(3-iodophenyl)isoxazole-3,4-dicarboxylate (2.42 g, 5.46 mmol) in dichloromethane (6 mL) at 0° C. was added TFA (6 mL). The mixture was warmed to ambient temperature and stirred for 4 hours. The reaction mixture was concentrated under vacuo to provide the mono carboxylic acid (2.10 g, 99%). To a solution of the mono acid (3.96 g, 10.2 mmol) in THF (20 mL) was added $Et_3N$ (4.84 mL, 34.8 mmol) at −20° C. After stirring 20 minutes methyl chloroformate (1.64 g, 17.4 mmol) was added at 0° C. After 30 minutes at 0° C. $NaBH_4$ (1.83 g, 48.2 mmol) was added portionwise and the resulting mixture stirred for 2 hours. Aqueous HCl (10%) was slowly added to the reaction mixture and the resulting mixture was extracted with ethyl acetate (2×200 mL). The combined organic layers were concentrated and the resulting residue purified by column chromatography (0–40% ethyl acetate in hexanes) to provide the titled compound (1.51 g, 40%).

Example 23E ethyl 4-((acetyloxy)methyl)-5-(3-iodophenyl)isoxazole-3-carboxylate

A solution of ethyl 4-(hydroxymethyl)-5-(3-iodophenyl)isoxazole-3-carboxylate (1.50 g, 4.03 mmol) in pyridine (5 mL) was stirred for 10 min. followed by cooling to 0° C. and slowly adding acetyl chloride (379 mg, 4.83 mmol). The mixture was allowed to come to ambient temperature and stirred for 2 hours. The solvent was removed under vacuo and the mixture purified by column chromatography (0–30% ethyl acetate in hexanes) to provide the titled compound (1.65 g, 99%).

Example 23F ethyl 4-((acetyloxy)methyl)-5-{3-((1E)-3-hydroxyprop-1-enyl)phenyl}isoxazole-3-carboxylate To a solution of ethyl 4-((acetyloxy)methyl)-5-(3-iodophenyl)isoxazole-3-carboxylate (1.43 g, 3.44 mmol) in DMF (4 mL) purged with $N_2$ was added $Pd_2(dba)_3$ (73 mg, 0.079 mmol), tri-2-furylphosphine (74 mg, 0.32 mmol), and CuI (30 mg, 0.16 mmol). The mixture was stirred for 20 minutes followed by the addition of 3-tributylstannyl-1-propenol (1.43 g, 4.12 mmol) in DMF (2 mL). After stirring for 16 hours the mixture was poured into $H_2O$ (100 mL) and extracted in t-butyl methyl ether (2×150 mL). The combined organic layers were dried (Na2SO4), filtered and concentrated under vacuo and the residue was purified by column chromatography 20–50% (ethyl acetate in hexanes) to provide the titled compound (978 mg, 82%).

Example 23G ethyl 4-((acetyloxy)methyl)-5-(3-{(1E)-3-(3-hydroxy-2-(methoxycarbonyl)phenoxy)prop-1-enyl}phenyl)isoxazole-3-carboxylate To a solution of ethyl 4-((acetyloxy)methyl)-5-{3-((1E)-3-hydroxyprop-1-enyl)phenyl}isoxazole-3-carboxylate (960 mg, 2.78 mmol) in THF (14 mL) was added methyl dihydroxybenzoate (934 mg, 5.57 mmol) and $PPh_3$ (1.46 g, 5.57 mmol). After purging the vessel with $N_2$, diethyazodicarboxylate (968 mg, 5.57 mmol) was added. The mixture was stirred for 16 hours, concentrated under vacuo and the residue purified by column chromatography (0–40% ethyl acetate in hexanes) to provide the titled compound (590 mg, 43%).

Example 23H

5-(3-{(1E)-3-(3-hydroxy-2-(methoxycarbonyl)phenoxy)prop-1-enyl}phenyl)-4-(hydroxymethyl)isoxazole-3-carboxylic acid To a solution of ethyl 4-((acetyloxy)methyl)-5-(3-{(1E)-3-(3-hydroxy-2-(methoxycarbonyl)phenoxy)prop-1-enyl}phenyl)isoxazole-3-carboxylate (190 mg, 0.38 mmol) in EtOH (1.5 mL) was added 1 mL THF and 3 mL aqueous $K_2CO_3$ (sat'd). After 1.5 hour at ambient temperature 4 M HCl was added until $CO_2$ evolution ceased. A precipitate formed which was filtered and dissolved in DMSO for purification by reverse phase HPLC (0–70% acetonitrile in 0.1% aqueous TFA) to provide the titled compound (100 mg, 61%). $^1H$ NMR (300 MHz, DMSO-$d_6$) δ 9.98 (s, 1H), 7.94 (broad s, 1H), 7.77 (broad d, J=7.8 Hz, 1H), 7.69 (broad d, J=7.8 Hz, 1H), 7.58 (t, J=7.8 Hz, 1H), 7.19 (t, J=8.3 Hz, 1H), 6.81 (broad d, J=16 Hz, 1H), 6.60 (d, J=8.3 Hz, 1H), 6.57 (dt, J=16, 5.2 Hz, 1H), 6.51 (d, J=8.3 Hz, 1H), 4.75 (d, J=5.2 Hz, 2H), 4.65 (s, 2H), 3.78 (s, 3H). MS (ESI+) m/z 426 $(M+H)^+$, 443 $(M+NH_4)^+$, 448 $(M+Na)^+$: (ESI−) m/z 424 $(M-H)^-$, 380 $(M-CO_2H)^-$.

What is claimed is:

1. A compound of formula (II),

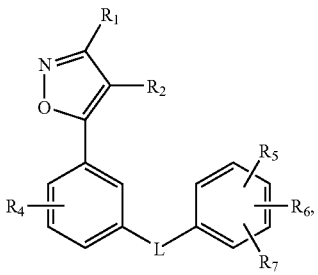

or a pharmaceutically suitable salt or prodrug thereof, wherein $R_1$ is a member selected from the group consisting of alkyl, alkoxy, alkylSO$_2$, trifluoroalkylSO$_2$, trifluoroalkylNH—, alkylSO$_2$NH—, carboxy, cyano, HONHcarbonyl, $R_a$ONHcarbonyl, nitro, $R_a$OC(O)—, HO$_3$S—, H$_2$NO$_2$S—, $R_a$NHO$_2$S—, (HO)$_2$(O)P—, (HO)$_2$(O)PCH$_2$—, (HO)$_2$(O)PCHF—, (HO)$_2$(O)PCF$_2$— and heterocycle, wherein said heterocycle is a member selected from the group consisting of:

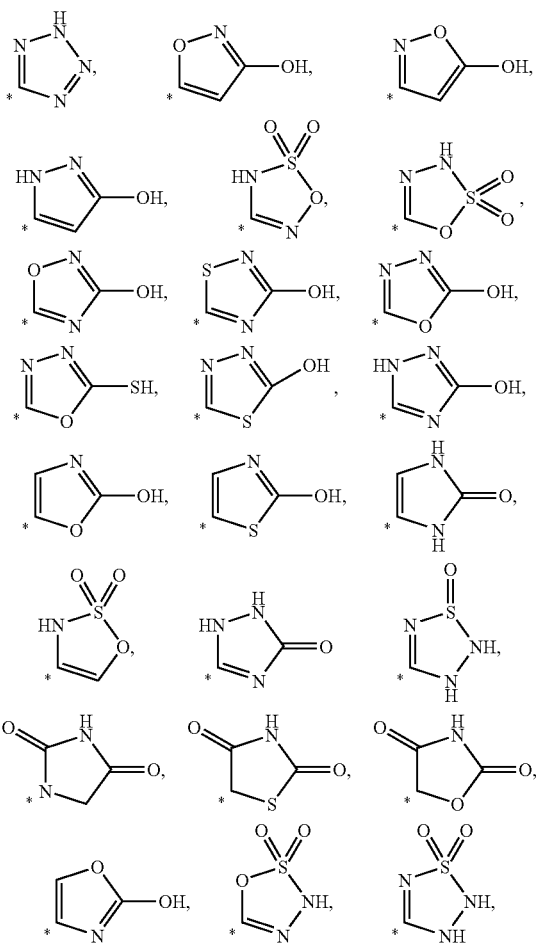

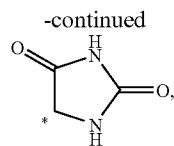

$R_3$, $R_4$, $R_5$, $R_6$ and $R_7$ are each independently absent or are independently a member selected from the group consisting of hydrogen, alkyl, alkylcarbonyl, alkoxy, alkoxyalkyl, alkoxycarbonyl, aryl, arylcarbonyl, arylalkyl, carboxy, carboxyalkyl, cyano, cycloalkyl, cycloalkylalkyl, halo, haloalkyl, heterocycle, heterocyclecarbonyl, heterocyclealkyl, hydroxy, hydroxyalkyl, nitro, trihaloalkyl, $R_aR_bN$, $R_aR_b$Nalkyl, $R_aR_b$Ncarbonyl, $R_aR_b$Ncarbonylalkyl, $R_aR_b$NNsulfonyl, $R_aR_b$NNsulfonylalkyl, wherein $R_a$ and $R_b$ are each independently a member selected from the group consisting of hydrogen, alkyl, alkoxycarbonyl, alkylcarbonyl, aryl, arylalkyl, cycloalkyl, cycloalkylalkyl, heterocycle, and heterocyclealkyl;

L is -G-X$_1$-J-X$_2$—K—;

G, J and K are independently a member selected from the group consisting of a bond, alkyl, alkenyl, aryl and cycloalkyl, wherein said alkyl, alkenyl, aryl and cycloalkyl may be optionally substituted with a group consisting of alkoxy, alkyl, halogen, hydroxy, hydroxyalkyl, carboxy and $R_dR_eN$—, wherein $R_d$ and $R_e$ are each independently a member selected from the group consisting of hydrogen, alkyl, alkoxycarbonyl, alkylcarbonyl and arylalkyl;

$X_1$ and $X_2$ are each independently a member selected from the group consisting of a bond, —O—, —N(R$_c$)—, —N(R$_c$)C(O)—, —C(O)N(R$_c$)—, —N(R$_c$)S(O)$_2$—, —S(O)$_2$N(R$_c$)—, and —C(O)—, wherein R$_c$ is a member selected from the group consisting of hydrogen, alkyl and arylalkyl, provided that both $X_1$ and $X_2$ are not a bond; and provided that if J is absent, then at least one of $X_1$ and $X_2$ must be absent.

2. The compound according to claim 1, wherein
G is a member selected from the group consisting of alkyl, alkenyl and cycloalkyl.

3. The compound according to claim 2, wherein
G is a member selected from the group consisting of alkyl, alkenyl and cycloalkyl; and
$X_1$, J and K are a bond.

4. The compound according to claim 1, wherein
G is a member selected from the group consisting of alkyl, alkenyl and cycloalkyl; and
$X_1$, J and K are a bond; and
$R_1$ is CO$_2$H.

5. The compound according to claim 4, a member selected from the group consisting of
5-(3-((1E)-3-(3-hydroxy-2-(methoxycarbonyl)phenoxy)prop-1-enyl)phenyl)isoxazole-3-carboxylic acid;
5-(3-(3-(3-hydroxy-2-(methoxycarbonyl)phenoxy)butyl)phenyl)isoxazole-3-carboxylic acid;
5-(3-((2-(3-hydroxy-2-(methoxycarbonyl)phenoxy)ethyl)amino)phenyl)isoxazole-3-carboxylic acid;
5-(3-(3-(3-hydroxy-2-(methoxycarbonyl)phenoxy)propyl)phenyl)isoxazole-3-carboxylic acid;
5-(2-fluoro-5-((1E)-3-(3-hydroxy-2-(methoxycarbonyl)phenoxy)prop-1-enyl)phenyl)isoxazole-3-carboxylic acid;

5-(3-((1E)-3-(3-hydroxy-2-nitrophenoxy)prop-1-enyl)phenyl)isoxazole-3-carboxylic acid;

5-(3-((1S,2S)-2-((3-hydroxy-2-(methoxycarbonyl)phenoxy)methyl)cyclopropyl)phenyl)isoxazole-3carboxylic acid;

5-(3-(3-(3-hydroxy-2-(methoxycarbonyl)phenoxy)butyl)-4-methoxyphenyl)isoxazole-3-carboxylic acid; 5-(4-fluoro-3-(3-(3-hydroxy-2-(methoxycarbonyl)phenoxy)butyl)phenyl)isoxazole-3-carboxylic acid;

5-(3-(3-(3-hydroxy-2-(methoxycarbonyl)phenoxy)pentyl)phenyl)isoxazole-3-carboxylic acid;

5-(3-((1E)-3-(3-hydroxy-2-propionylphenoxy)prop-1-enyl)phenyl)isoxazole-3-carboxylic acid;

5-(3-((1E)-4-hydroxy-3-(3-hydroxy-2-(methoxycarbonyl)phenoxy)but-1-enyl)phenyl)isoxazole-3-carboxylic acid;

5-(1-(2-(3-hydroxy-2-(methoxycarbonyl)phenoxy)ethyl)-1H-indol-6-yl)isoxazole-3-carboxylic acid;

5-(3-((1E)-3-(2-(acetylamino)-3-hydroxyphenoxy)prop-1-enyl)phenyl)isoxazole-3-carboxylic acid;

5-(3-((1E)-3-(2-((benzylamino)carbonyl)-3-hydroxyphenoxy)prop-1-enyl)phenyl)isoxazole-3-carboxylic acid;

5-(3-((1E)-3-(3-hydroxy-2-(methoxycarbonyl)-4-nitrophenoxy)prop-1-enyl)phenyl)isoxazole-3-carboxylic acid;

4-amino-5-(3-((1E)-3-(3-hydroxy-2-(methoxycarbonyl)phenoxy)prop-1-enyl)phenyl)isoxazole-3-carboxylic acid;

5-(3-((1E)-3-((3',5-dihydroxy-4-(methoxycarbonyl)- 1,1'-biphenyl-3-yl)oxy)prop-1-enyl)phenyl)isoxazole-3-carboxylic acid; and 5-(3-{(1E)-3-(3-hydroxy-2-(methoxycarbonyl)phenoxy)prop- 1-enyl }phenyl)-4-(hydroxymethyl)isoxazole-3-carboxylic acid.

6. The compound according to claim 1, wherein $X_1$ is a member selected from the group consisting of —NH— and —NHC(O)—.

7. The compound according to claim 1, wherein $X_1$ is a member selected from the group consisting of —NH— and —NHC(O)—; and G and K are a bond.

8. The compound according to claim 1, wherein $X_1$ is a member selected from the group consisting of —NH— and NHC(O)—;

G and K are a bond; and $R_1$ is $CO_2H$.

9. The compound according to claim 8, a member selected from the group consisting of 5-(3-(((1-acetylpiperidin-4-yl)carbonyl)amino)phenyl)isoxazole-3-carboxylic acid;

5-(3-((2-(3-hydroxy-2-((methylamino)carbonyl)phenoxy)ethyl)amino)phenyl)isoxazole-3-carboxylic acid; and 5-(3-((1E)-3-(3-hydroxy-2-((methylamino)carbonyl)phenoxy)prop-1-enyl)phenyl)isoxazole-3-carboxylic acid.

10. The compound according to claim 1 wherein

L is a bond; and $R_1$ is $CO_2H$.

11. The compound according to claim 10 that is

5-{3'-(3-(carboxy)isoxazol-5-yl)-1,1'-biphenyl-3-yl}isoxazole-3-carboxylic acid.

12. A pharmaceutical composition comprising a therapeutically effective amount of a compound of claim 1 in combination with a pharmaceutically suitable carrier.

\* \* \* \* \*